(12) United States Patent
Dumont et al.

(10) Patent No.: US 11,384,130 B2
(45) Date of Patent: Jul. 12, 2022

(54) AGENT FOR PROMOTING ANGIOGENESIS AND METHODS AND USES THEREOF

(71) Applicants: Vasomune Therapeutics Inc., Toronto (CA); Sunnybrook Research Institute, Toronto (CA)

(72) Inventors: Daniel Dumont, Oakville (CA); Paul van Slyke, North York (CA); David Tumelty, Rancho Palos Verdes, CA (US); Kenneth Sokoll, Manotick Place (CA); Jason Moss, Petaluma, CA (US)

(73) Assignees: Vasomune Therapeutics Inc., Toronto (CA); Sunnybrook Research Institute, Toronto (CA)

( * ) Notice: Subject to any disclaimer, the term of this patent is extended or adjusted under 35 U.S.C. 154(b) by 297 days.

(21) Appl. No.: 16/476,750

(22) PCT Filed: Jan. 11, 2018

(86) PCT No.: PCT/CA2018/050022
§ 371 (c)(1),
(2) Date: Jul. 9, 2019

(87) PCT Pub. No.: WO2018/129618
PCT Pub. Date: Jul. 19, 2018

(65) Prior Publication Data
US 2019/0359670 A1    Nov. 28, 2019

Related U.S. Application Data

(60) Provisional application No. 62/446,030, filed on Jan. 13, 2017.

(51) Int. Cl.
| | |
|---|---|
| *C07K 14/515* | (2006.01) |
| *A61P 31/16* | (2006.01) |
| *A61K 38/18* | (2006.01) |
| *A61K 47/60* | (2017.01) |
| *A61K 31/13* | (2006.01) |
| *A61K 31/351* | (2006.01) |
| *A61K 31/196* | (2006.01) |
| *A61K 31/7056* | (2006.01) |
| *A61K 31/215* | (2006.01) |

(52) U.S. Cl.
CPC ............ *C07K 14/515* (2013.01); *A61K 31/13* (2013.01); *A61K 31/196* (2013.01); *A61K 31/215* (2013.01); *A61K 31/351* (2013.01); *A61K 31/7056* (2013.01); *A61K 38/1891* (2013.01); *A61K 47/60* (2017.08); *A61P 31/16* (2018.01)

(58) Field of Classification Search
None
See application file for complete search history.

(56) References Cited

U.S. PATENT DOCUMENTS

| | | | | |
|---|---|---|---|---|
| 8,957,022 | B2 * | 2/2015 | Van Slyke | A61K 38/08 |
| | | | | 514/7.5 |
| 9,186,390 | B2 * | 11/2015 | Van Slyke | A61K 47/60 |
| 10,314,882 | B2 * | 6/2019 | Dumont | A61K 38/10 |

FOREIGN PATENT DOCUMENTS

| | | |
|---|---|---|
| WO | 2008/049227 A1 | 5/2008 |
| WO | 2011/134056 A1 | 4/2011 |
| WO | 2014/165963 A1 | 10/2014 |
| WO | WO 2014/165963 | * 10/2014 |

OTHER PUBLICATIONS

Jain et al. (Pharm Res. 2015; 32(11): 3526-3540) (Year: 2015).*
Sugiyama et al., "The Tie2-agonist Vasculotide rescues mice from influenza virus infection", Scientific Reports, 5:11030, Jun. 5, 2015. Retrieved from: https://www.nature.com/articles/srep11030. <DOI: 10:1038/srep11030>.
Bourdeau et al., "Vasculotide, an Angiopoietin-1 mimetic, ameliorates several features of experimental atopic dermatitis-like disease", BMC Res. Notes, May 28, 2016 (May 28, 2016), vol. 9, pp. 289, ISSN 12756-0500. <DOI: 10:1186/s13104-015-1817-1 >.
Wu et al., "A novel small peptide as a targeting ligand for receptor tyrosine kinase Tie2", Biochemical and Biophysical Research Communications 315 (2004) 1004-1010, Jan. 15, 2004. <DOI: I0.1016/j.bbrc.2004.01.157>.
Van Slyke et al., "Acceleration of Diabetic Wound Healing by an Angiopoietin Peptide Mimetic", Tissue Engineering: Part A, vol. 15, pp. 1269-1280, Nov. 6, 2009. <DOI: 10.1089=ten.tea.2007.0400>.
Tournaire et al., "A short synthetic peptide inhibits signal transduction, migration and angiogenesis mediated by Tie2 receptor", EMBO Reports, vol. 5, No. 3, 262-267, Feb. 20, 2004. <DOI: 10.1038/sj.embro.7400100>.
Rubig et al., "The Synthetic Tie2 Agonist Peptide Vasculotide Protects Renal Vascular Barrier Function in Experimental Acute Kidney Injury", Scientific Reports, 6:22111, Feb. 25, 2016. <DOI: 10.1038/srep22111>.
Allowable Claims of European Patent Application No. 18738716.2.
Official Action dated Dec. 13, 2021 of European Patent Application No. 18738716.2.

* cited by examiner

*Primary Examiner* — Sergio Coffa
(74) *Attorney, Agent, or Firm* — Much Shelist, PC; Christopher M. Cabral

(57) ABSTRACT

The present disclosure relates to compounds of Formula (I) which are multimeric forms of a monomeric binding peptide linearly bonded to PEG moieties to form the multimers. The multimeric forms stimulate angiogenesis and promote wound healing. The disclosure also includes pharmaceutical compositions comprising the multimers, including compositions suitable for topical or systemic administration.

26 Claims, 13 Drawing Sheets

Specification includes a Sequence Listing.

Figure 2E
Human IgGFC with Parental VT
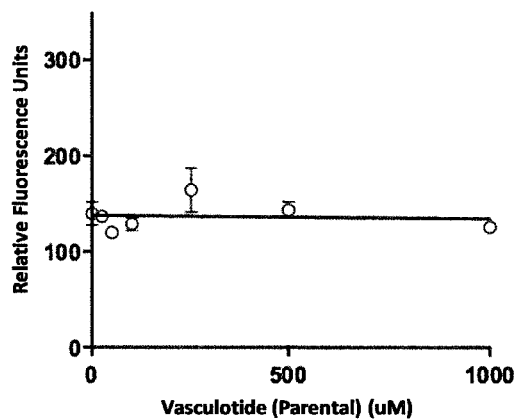
Figure 2F
Human IgGFC with MPA-Br
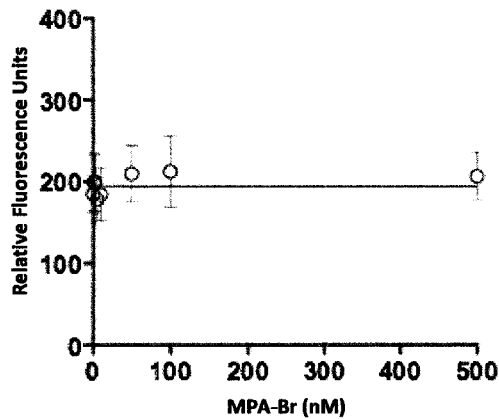
Figure 2G
| | Species Tie2FC + parental VT or MPA-Br | Kd |
|---|---|---|
| 1 | Human+parental VT 95% CI | 102.9 nM |
| 2 | Mouse+parental VT 95% CI | 34.95 nM |
| 3 | Human+MPA-Br 85% CI | 2.623 nM |
| 4 | Mouse+MPA-Br 95% CI | 6.815 nM |
| 5 | Rat+MPA-Br 85% CI | 4.213 nM |
| 6 | Cyno+MPA-Br 72% CI | 22.91 pM |

SEQUENCE LISTING

<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

His His His Arg His Ser Phe
1               5

<210> SEQ ID NO 2
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 2

Trp Thr Ile Ile Gln Arg Arg Glu Asp Gly Ser Val Asp Phe Gln Arg
1               5                   10                  15

Thr Trp Lys Glu Tyr Lys
            20

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 3

Asn Leu Leu Met Ala Ala Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

```
-continued

<400> SEQUENCE: 4

Lys Leu Trp Val Ile Pro Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

His Pro Trp Leu Thr Arg His
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Cys His His His Arg His Ser Phe
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: N-terminus has an MpA

<400> SEQUENCE: 7

His His His Arg His Ser Phe
1               5
```

AGENT FOR PROMOTING ANGIOGENESIS AND METHODS AND USES THEREOF

CROSS-REFERENCE TO RELATED APPLICATIONS

This application is a National Phase Entry of International Application No. PCT/CA2018/050022 filed Jan. 11, 2018 (which designates the U.S.), which claims priority from U.S. provisional application No. 62/446,030 filed on Jan. 13, 2017, the contents of both of which are incorporated herein by reference in their entirety.

Incorporation of Sequence Listing

A computer readable form of the Sequence Listing "23632-P52201US01_SequenceListing.txt" (4096 bytes), submitted via EFS-WEB and created on Jul. 9, 2019, is herein incorporated by reference.

FIELD

The disclosure relates to an agent that has improved activity compared to vasculotide, and methods and uses thereof. In particular, the disclosure relates to methods and uses for stimulating angiogenesis to treat diabetic wound healing and other cardiovascular indications, for treating allergic diseases, asthma and atopic dermatitis, and for treating influenza.

BACKGROUND

Several key molecular players have been identified to regulate maintenance of vascular homeostasis. One of the best known of these is the Tie2/Angiopoietin (Ang) signaling axis. This receptor tyrosine kinase (Tie2) and protein growth factor (Ang) system is somewhat unique in that the two main growth factors, Ang1 and Ang2, propagate anti or pro-inflammatory responses respectively through the same receptor located on the vascular endothelium. Unlike most receptor tyrosine kinases, Tie2 is maintained in a constitutively active state in normal, healthy endothelial cells through the actions of Ang1. This receptor has been found to activate a number of intracellular pathways that regulate proliferation and endothelial cell survival (MAPK and AKT), permeability (VE-Cadherin) and cell-cell interactions (ICAM and VCAM), all of which during normal physiology work in concert to maintain endothelial cell quiescence. Activation of this pathway, marked by Tie2 receptor phosphorylation serves as a transdominant signal; opposing the induction of vascular leak following exposure to a myriad of inflammatory factors including VEGF, serotonin, bradykinin, histamine, PAF, thrombin, LPS, septic serum and anthrax toxin (Parikh S M, Virulence 2013). Precipitous rises in Ang2 levels have repeatedly been shown to result in vascular leakage, morbidity and mortality following a host of different insults. Studies have demonstrated that it is the balance between circulating levels of Ang1 and Ang2 that defines the dominant underlying state of vascular activation. Because of this fact, approaches aimed at modulating this pathway may have therapeutic applications.

The complex nature of the Angs has precluded purification and therapeutic application thus far. As such, alternative approaches to modulate this pathway have been examined extensively. Two main approaches have been described thus far. The first approach, and by far the more common, has focused on blocking the antagonistic ligand, Ang2. Therapeutics in this class can be roughly defined as blocking antibodies or peptibodies against Ang2. The second class of Tie2-targetted modulators borrows from the elucidated structural characteristics of Ang1. That is, that bioactive Ang1 exists naturally as a multimer of not less than four subunits. It is hypothesized that Ang1 subunits bind to the Tie2 receptor and in so doing cluster adjacent receptors; effectively juxtapositioning receptors in a configuration that facilitates transphosphorylation. To mimic the agonistic action of Ang1 for the Tie2 receptor, several large, recombinant proteins have been engineered which bind to and cluster adjacent receptors (Zhang et al. 2002; Cho et al. 2004; Han et al. 2016; U.S. Pat. No. 8,957,022).

Vasculotide (also called parental vasculotide) is a rationally designed, fully synthetic compound that mimics the actions of Ang1. The central core of Vasculotide consists of a 10 kDa, narrow dispersity, 4-armed polyethylene glycol. Covalent attachment of high affinity Tie2 binding peptides, in particular (—CHHHRHSF—, SEQ ID NO:6) is facilitated through reaction of activated malemide groups and the amino terminal cysteine. This structure has been defined as an optimal configuration to bind and activate the Tie2 receptor. Direct activation of Tie2 with parental Vasculotide has been shown to provide a dominant anti-vascular leak signal in several distinct in vitro and in vivo studies, including preclinical models of atopic disease and influenza (Bourdeau A, et al BMC Res Notes 2016 and Sugiyama M G, et al Sci Rep 2015).

Influenza-induced acute lung injury or the more severe and related diagnosis, acute respiratory distress syndrome (ALI/ARDS) exacts a heavy toll on the public each year, disproportionately effecting the young and elderly. A common, conserved feature of pathogen-mediated ALI/ARDS is the induction of vascular leak. Therapeutic approaches at treating the host's response to infection, specifically vascular leak, should not be fraught with the rapid development of resistance seen with therapeutics specifically aimed at ever-mutating pathogens. There are currently no therapeutically targeted approaches approved for the treatment of lung injury. The use of Tie2 agonists, such as Vasculotide, to treat influenza-induced ALI/ARDS may provide certain conceptual points of differentiation over the use of vaccines and/or antivirals. For example, current influenza vaccination programs require a priori knowledge related to strain identity, while resistance to antiviral medications has been well documented in recent history. In addition, the threat represented from emerging pathogenic strains or weaponized organisms could potentially render available therapeutics completely ineffective. As such, novel approaches to treating the host's response to pathogens are urgently needed.

SUMMARY

Chemical analysis of parental vasculotide revealed that the resulting peptide PEG conjugate contains a mixture of 5 and 6 membered ring products (FIG. 1A). The 5-membered succinimide ring shown results from the direct alkylation of maleimide by the thiol group on cysteine and the 6 membered thiazin ring also shown results from rearrangement of this initial product through the free amine group on the cysteine linker. These findings have led to the development of a simpler vasculotide analog (Mpa-Br) in which the peptide is linked to the PEG through a linear sulfane moiety to form the activated PEG tetramer. In one embodiment, the Mpa-Br is prepared by linkage of the T7 peptide with 3-Mercaptopropionic acid, an achiral analog of cysteine without the amine side chain at the N terminus to an activated PEG tetramer containing bromoacetimide (FIG.

1B). The resulting peptide PEG conjugate provides a single product free of labile ring structures susceptible to rearrangement.

Accordingly, the present disclosure provides a compound of formula (I),

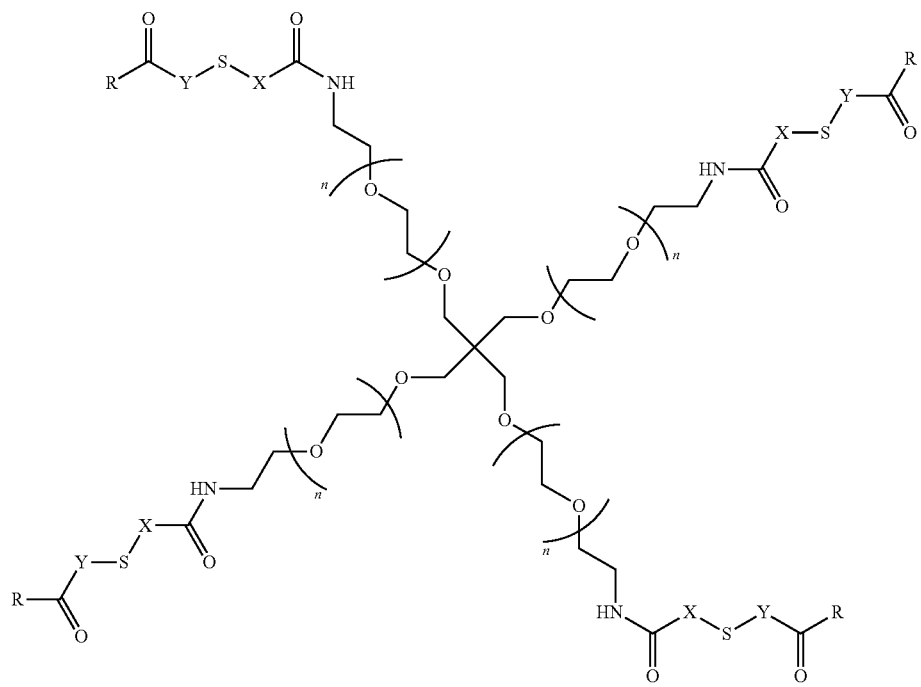

wherein
n is an integer from about 25 to about 100, each X is independently or simultaneously $(C_1-C_{20})$-alkylene or $(C_2-C_{20})$-alkenylene, each of which is optionally substituted with one or more of halo, amino, hydroxy, $(C_1-C_6)$-alkyl, $(C_1-C_6)$-alkoxy, $(C_6-C_{10})$-aryl, or $(C_5-C_{10})$-heteroaryl;
each Y is independently or simultaneously $(C_1-C_{20})$-alkylene or $(C_2-C_{20})$-alkenylene, each of which is optionally substituted with one or more of halo, amino, hydroxy, $(C_1-C_6)$-alkyl, $(C_1-C_6)$-alkoxy, $(C_6-C_{10})$-aryl, or $(C_5-C_{10})$-heteroaryl; and
R is a T7 peptide (SEQ ID NO:1), a GA3 peptide (SEQ ID NO:2), a T4 peptide (SEQ ID NO:3), a T6 peptide (SEQ ID NO:4) and/or a T8 peptide (SEQ ID NO:5) or a retro-inverso peptide thereof;
or a pharmaceutically acceptable salt thereof.

In an embodiment, the compound stimulates Tie 2 phosphorylation; phosphorylation of MAPK, AKT and/or eNOS; stimulates endothelial cell migration; stimulates MMP2 release from endothelial cells and protection of endothelial cells from serum withdrawal-induced apoptosis; stimulates an angiogenic response in vivo in a Matrigel assay; stimulates wound healing in a subject when applied topically to a wound of the subject; decreases vascular leak; treats allergic disease and/or treats influenza.

In an embodiment, R is a T7 peptide as shown in SEQ ID NO:1.

In an embodiment, herein provided is a pharmaceutical composition comprising the compound disclosed herein and a pharmaceutically acceptable carrier. In one embodiment, the pharmaceutically acceptable carrier is suitable for topical administration. In another embodiment, the pharmaceutically acceptable carrier is suitable for systemic administration. In yet another embodiment, the pharmaceutically acceptable carrier is suitable for intranasal administration, inhalation or as a component of perfusate.

Also provided herein is a method of making the compound of the formula (I) disclosed herein comprising (i) reacting a peptide which is T7 peptide (SEQ ID NO:1), a GA3 peptide (SEQ ID NO:2), a T4 peptide (SEQ ID NO:3), a T6 peptide (SEQ ID NO:4) and/or a T8 peptide (SEQ ID NO:5), or a retro-inverso peptide thereof, with a thiol compound of the formula (II)

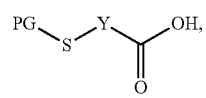

to obtain a compound of the formula (III)

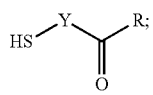

(ii) reacting the compound of the formula (III) with a PEG-tetramer of the formula (IV)

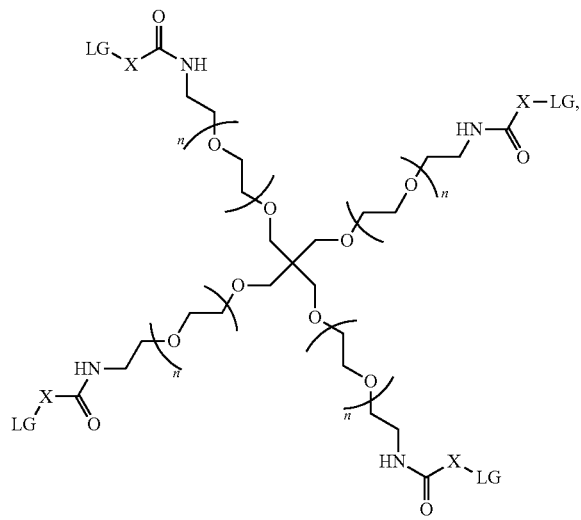

to obtain a compound of the formula (I),
wherein the variables n, X and Y are as defined above, LG is a suitable leaving group and PG is H or a suitable protecting group.

Also provided herein is a method of activating a Tie 2 receptor comprising contacting the Tie 2 receptor with the compound disclosed herein such that the Tie 2 receptor is activated. In an embodiment, activation of the Tie 2 receptor is evidenced by phosphorylation of tyrosine residues, such as tyrosine 992 (Y992) in humans and Y990 for mice, of the Tie 2 receptor or by phosphorylation of MAPK, AKT or eNOS.

Even further provided is a method of stimulating angiogenesis in a subject comprising administering the compound disclosed herein to the subject in need thereof.

In another embodiment, angiogenesis stimulated by the compound is characterized by at least one of the following properties:
   a) recruitment of perivascular support cells;
   b) non-leakiness of vessels that would otherwise be leaky;
   c) well-defined arborization; and
   d) inhibition of endothelial cell apoptosis.

In another embodiment, the method further comprises administering a second angiogenic agent concurrently or sequentially. In one embodiment, the second angiogenic agent is VEGF. In another embodiment, the second angiogenic agent is selected from the group consisting of PDGF, G-CSF, recombinant human erythropoietin, bFGF, Ang2 inhibitor and placental growth factor (PLGF).

In yet a further embodiment, the subject in need thereof has a clinical condition selected from vascularization of regenerative tissues, ischemic limb disease, cerebral ischemia, conditions of vascular inflammation, arteriosclerosis, avascular necrosis, stimulation of hair growth and erectile dysfunction.

Also provided herein is a method of decreasing vascular permeability at a site of leaky vessels comprising administering the compound disclosed herein to the site in a subject in need thereof. In an embodiment, the subject has or had a stroke, macular degeneration, macular edema, lymph edema, breakdown of the blood-retinal barrier, breakdown of the blood-brain barrier, bacterial induced vascular leak, or normalization of tumor vasculature.

Also provided herein is a method of protecting endothelial cells comprising administering the compound disclosed herein to a subject in need thereof. In one embodiment, the subject has or had kidney injury or kidney fibrosis, stroke, vascular dementia, macular degeneration or diabetic complications. In another embodiment, the subject has or had a lung injury.

Even further provided is a method of stimulating healing of a wound comprising administering the compound disclosed herein to a wound in a subject in need thereof. In an embodiment, the compound is administered topically or systemically. In one embodiment, the wound is a diabetic ulcer. In another embodiment, the wound is a decubitus ulcer, a pressure ulcer, a surgical incision, a traumatic tissue injury, a burn or a skin graft.

Yet further provided herein is a method of inhibiting the expansion of CFU-G cells comprising administering the compound disclosed herein to a subject in need thereof. In an embodiment, the method is for reducing eosinophils and/or basophils in the subject in need thereof, for treating atopic dermatitis, asthma or allergic rhinitis, or for treating a condition associated with eosinophils and/or basophils in the subject in need thereof.

In one embodiment, the condition associated with eosinophils and/or basophils is leukemia of eosinophil and/or basophil origin. In another embodiment, the condition associated with eosinophils and/or basophils is inflammatory bowel disease. In yet another embodiment, the condition associated with eosinophils and/or basophils is a parasitic infection.

In another embodiment, the method of inhibiting the expansion of CFU-G cells is for reducing inflammatory cytokine and/or chemokine levels comprising at least one of eotaxin, IL-17, MIG, IL12/IL23 (p40), IL-9, MIP-1a, MIP-1b, RANTES, TNF-α, IL-1β, IL-5, IL-13, and MCP-1. In one embodiment, the inflammatory cytokine and/or chemokine comprises eotaxin.

In another embodiment, the method inhibits histamine induced vascular leak.

Even further provided herein is a method of treating a subject infected with influenza or with a bacterial superinfection associated with influenza comprising administering the compound disclosed herein to the subject in need thereof.

In one embodiment, the method further comprises administering an antiviral agent concurrently or sequentially. In an embodiment, the antiviral agent is amantadine, rimantadine, zanamivir, peramivir, viramidine, ribavirin or oseltamivir. In another embodiment, the subject is human and the influenza is human influenza.

In an embodiment, the compound is administered topically, systemically, intranasally, by inhalation or as a perfusate.

Also provided is a composition comprising (a) a compound disclosed herein and (b) an antiviral agent. Even further provided is a composition comprising (a) a compound disclosed herein and (b) an angiogenic agent.

Further provided is a kit comprising (a) a compound disclosed herein, (b) a second angiogenic agent and (c) instructions for use of the kit for activating Tie2 and/or for stimulating angiogenesis as disclosed herein.

Further provided is a kit comprising (a) a compound disclosed herein, (b) an antiviral agent and (c) instructions for use of the kit for treating an subject infected with influenza and/or for treating a bacterial superinfection in a subject infected with influenza.

Even further provided is a biomaterial into which is incorporated the compound disclosed herein. In one embodiment, the biomaterial is Matrigel, a skin substitute or a cross-linked glycosaminoglycan hydrogel. In another embodiment, a second agent is incorporated into the biomaterial, such as VEGF, PDGF, G-CSF, recombinant human erythropoietin, bFGF and placental growth factor (PLGF).

Other features and advantages of the present disclosure will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

Embodiments are described below in relation to the drawings in which:

FIG. 2E shows binding curves of parental Vasculotide with human IgGFc. FIG. 2F shows binding curves of MPA-Br with human IgGFc. No saturation of binding is observed with human IgGFc and parental Vasculotide or human IgGFc and MPA-Br. FIG. 2G shows a table depicting the binding constants of parental Vasculotide and MPA-Br for various species of recombinant Tie2FC. Tryptophan scanning fluorescent spectroscopy was used to determine the binding constants of parental Vasculotide and MPA-Br for indicated species of recombinant Tie2Fc receptor.

DETAILED DESCRIPTION

Definitions

Figure 1A:
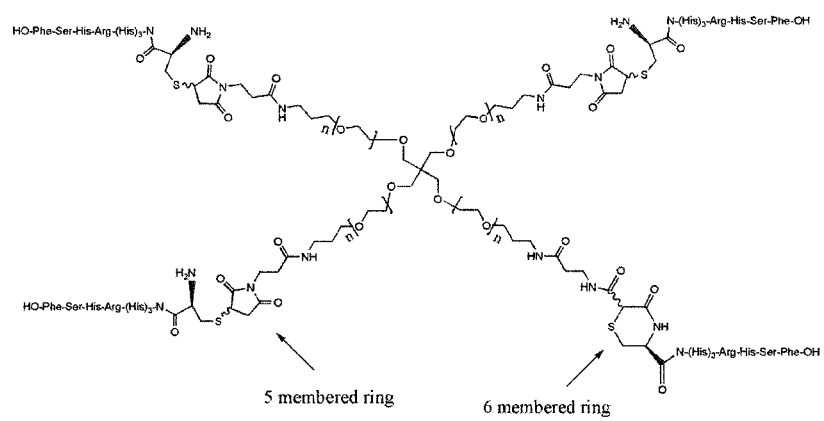
FIG. 1A shows a schematic diagram of parental Vasculotide, prepared via linkage of the T7 peptide with cysteine at the N terminus to an activated PEG tetramer containing Maleimide. The resulting peptide PEG conjugate contains a mixture of 5 and 6 membered ring products. The 5-membered succinimide ring shown results from the direct alkylation of maleimide by the thiol group on cysteine and the 6 membered thiazin ring also shown results from rearrangement of this initial product through the free amine group on the cysteine linker.
Figure 1B:
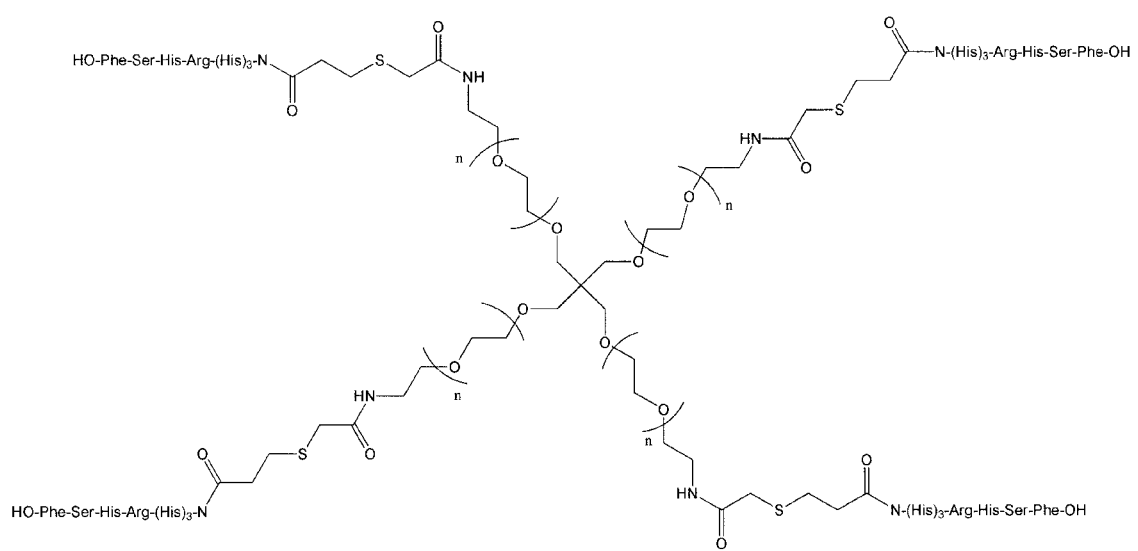
FIG. 1B shows a schematic diagram of Mpa-Br, prepared, in one embodiment, by linkage of the T7 peptide with 3-Mercaptopropionic acid, an achiral analog of cysteine without the amine side chain at the N terminus to an activated PEG tetramer containing bromoacetimide.

The term "$(C_1-C_p)$-alkyl" as used herein means straight and/or branched chain, saturated alkyl radicals containing from one to "p" carbon atoms and includes (depending on the identity of p) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical.

The term "$(C_2-C_p)$-alkenyl" as used herein means straight and/or branched chain, unsaturated alkyl moieties containing from two to "p" carbon atoms and includes at least one carbon-carbon double bond and includes (depending on the identity of p) ethenyl, 1-propenyl, isopropenyl, 1-butenyl, 2-butenyl, t-butenyl, 1-pentenyl, 2-methyl-1-pentenyl, 3-methyl-1-pentyl, 4-methyl-1-pentyl, 1-hexenyl, 2-hexenyl and the like, where the variable p is an integer representing the largest number of carbon atoms in the alkenyl radical.

The term "$(C_1-C_p)$-alkoxy" means an alkyl group, as defined above, having an oxygen atom attached thereto. As used herein, the term means straight and/or branched chain, saturated alkyl radicals having an oxygen atom attached thereto and containing from one to "p" carbon atoms and includes (depending on the identity of p) methoxy, ethoxy, propoxy, isopropoxy, n-butoxy, s-butoxy, isobutoxy, t-butoxy, 2,2-dimethylbutoxy, n-pentoxy, 2-methylpentoxy, 3-methylpentoxy, 4-methylpentoxy, n-hexoxy and the like, where the variable p is an integer representing the largest number of carbon atoms in the alkoxy radical.

The term "aryl" as used herein refers to cyclic groups that contain at least one aromatic ring, for example a single ring (e.g. phenyl) or multiple condensed rings (e.g. naphthyl). In an embodiment of the present disclosure, the aryl group contains 6, 9 or 10 atoms such as phenyl, naphthyl, indanyl, anthracenyl, 1,2-dihydronaphthyl, 1,2,3,4-tetrahydronaphthyl, fluorenyl, indanyl, indenyl and the like.

The term "heteroaryl" as used herein refers to aromatic cyclic or polycyclic ring systems having at least one heteroatom chosen from N, O and S and at least one aromatic ring. Examples of heteroaryl groups include, without limitation, furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl and quinazolinyl, among others The term "halo" as used herein refers to a halogen atom and includes fluorine (F), chlorine (Cl), bromine (Br) and iodine (I).

The suffix "ene" added on to any of the above groups means that the group is divalent, i.e. inserted between two other groups.

A retro-inverso peptide as used herein refers to a peptide where d-amino acids are substituted in reverse sequence. Side chain topology would mimic the original molecule (primary structure) and thus provides for binding.

Compounds of the Disclosure

In one embodiment, the present inventors provide a class of novel agents that have improved activity over vasculotide (VT) and refer to one of the novel agents in the Examples as "Mpa-Br".

Accordingly, the present disclosure provides a compound of formula (I),

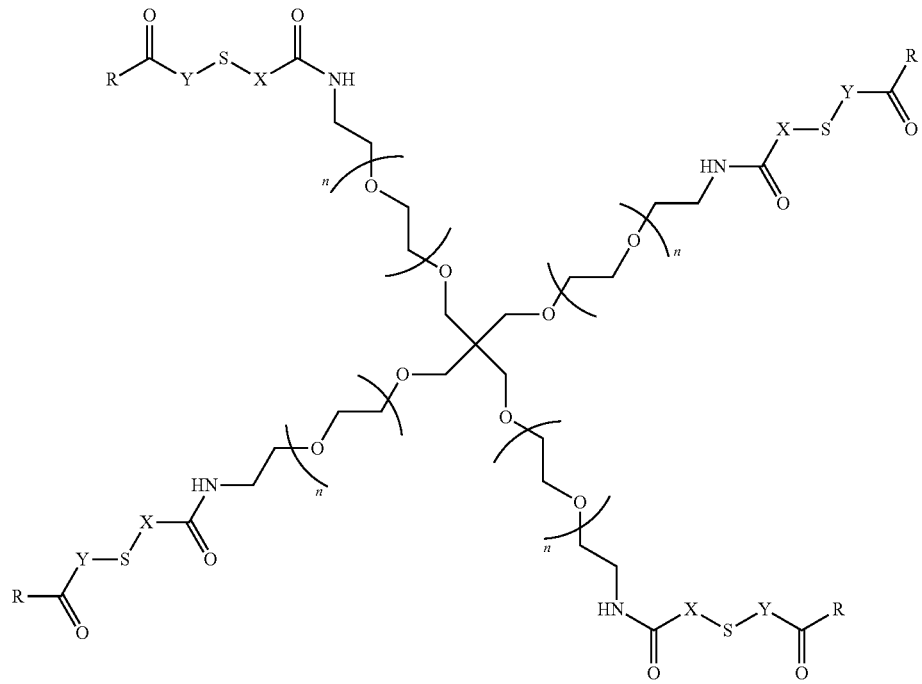

wherein n is an integer from about 25 to about 100, each X is independently or simultaneously $(C_1-C_{20})$-alkylene or $(C_2-C_{20})$-alkenylene, each of which is optionally substituted with one or more of halo, amino, hydroxy, $(C_1-C_6)$-alkyl, $(C_1-C_6)$-alkoxy, $(C_6-C_{10})$-aryl, or $(C_5-C_{10})$-heteroaryl;

each Y is independently or simultaneously $(C_1-C_{20})$-alkylene or $(C_2-C_{20})$-alkenylene, each of which is optionally substituted with one or more of halo, amino, hydroxy, $(C_1-C_6)$-alkyl, $(C_1-C_6)$-alkoxy, $(C_6-C_{10})$-aryl, or $(C_5-C_{10})$-heteroaryl; and R is a T7 peptide (SEQ ID NO:1), a GA3 peptide (SEQ ID NO:2), a T4 peptide (SEQ ID NO:3), a T6 peptide (SEQ ID NO:4) or a T8 peptide (SEQ ID NO:5) or a retro-inverso peptide thereof;

and/or a pharmaceutically acceptable salt thereof.

In one embodiment, R is a T7 peptide, which T7 peptide comprises an amino acid sequence: His-His-His-Arg-His-Ser-Phe (SEQ ID NO: 1). In another embodiment, R is a GA3 peptide, which GA3 peptide comprises an amino acid sequence: Trp-Thr-Ile-Ile-Gln-Arg-Arg-Glu-Asp-Gly-Ser-Val-Asp-Phe-Gln-Arg-Thr-Trp-Lys-Glu-Tyr-Lys (SEQ ID NO: 2). In another embodiment, R is a T4 peptide, which T4 peptide comprises an amino acid sequence: Asn-Leu-Leu-Met-Ala-Ala-Ser (SEQ ID NO: 3). In yet another embodiment, R is a T6 peptide, which T6 peptide comprises an amino acid sequence: Lys-Leu-Trp-Val-Ile-Pro-Lys (SEQ ID NO: 4). In yet another embodiment, R is a T8 peptide, which T8 peptide comprises an amino acid sequence: His-Pro-Trp-Leu-Thr-Arg-His (SEQ ID NO: 5).

T4, T6, T7 and T8 are Tie 2 binding peptides T4, T6, T7 and T8 described in Tournaire, R. et al. (2004) *EMBO Reports* 5:262-267. GA3 is also a Tie 2 binding peptide described in Wu, X. et al. (2004) *Biochem. Biophys. Res. Commun.* 315:1004-1010.

In one embodiment, n is an integer from about 40 to about 70, or about 48 to about 65, or about 55.

In another embodiment, X is independently or simultaneously $(C_1-C_{10})$-alkylene or $(C_2-C_{10})$-alkenylene. In another embodiment, X is independently or simultaneously $(C_1-C_6)$-alkylene or $(C_2-C_6)$-alkenylene. In another embodiment, X is independently or simultaneously $(C_1-C_3)$-alkylene. In another embodiment, X is methylene ($—CH_2—$). In another embodiment, the optional substituents are one or more of halo or $(C_1-C_3)$-alkyl, or $CH_3$.

In another embodiment, Y is independently or simultaneously $(C_1-C_{10})$-alkylene or $(C_2-C_{10})$-alkenylene. In another embodiment, Y is independently or simultaneously $(C_1-C_6)$-alkylene or $(C_2-C_6)$-alkenylene. In another embodiment, Y is independently or simultaneously $(C_1-C_3)$-alkylene. In another embodiment, Y is ethylene ($—CH_2CH_2—$). In another embodiment, Y is derived from thioglycolic acid, 2-Mercaptopropionic acid, 4-Mercaptobutyric acid, 6-Mercaptohexanoic acid, 8-Mercaptooctanic acid, 11-Mercaptoundecanoic acid, 12-Mercaptododecanoic acid, or 16-Mercaptohexadecanoic acid.

In one embodiment, the compound of the formula (I) is

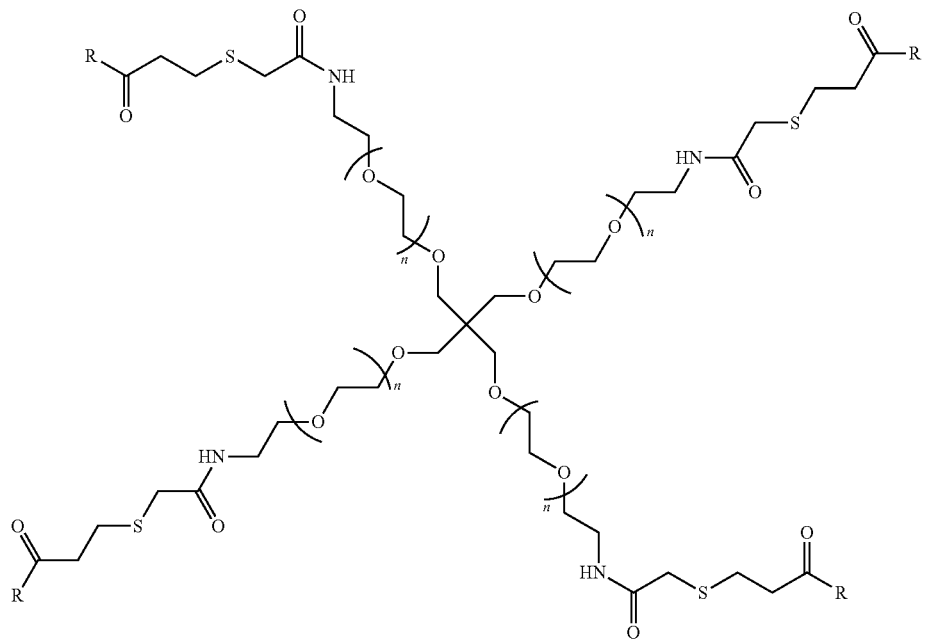

wherein n is an integer between about 50-60 or about 55; and

R is His-His-His-Arg-His-Ser-Phe (SEQ ID NO: 1);

or a pharmaceutically acceptable salt thereof.

In another embodiment, the pharmaceutically acceptable salt is an acid addition salt such as an acetate, trifluoroacetate or HCl salt form. In another embodiment, the compound of formula (I) is a salt which is the acetate or hydrochloride salt.

In other embodiments, the present disclosure also includes dimers and trimers, in addition to the tetramers of the compounds of formula (I). In one embodiment, the disclosure includes dimer, trimer and tetramer compounds having the formula

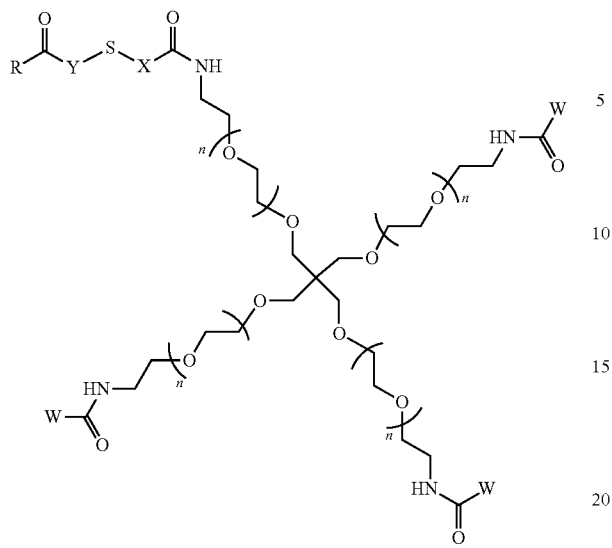

wherein

W is independently or simultaneously hydroxy-substituted $(C_1$-$C_{20})$-alkyl or hydroxy-substituted $(C_2$-$C_{20})$-alkenyl, each of which is optionally substituted with one or more of halo, amino, hydroxy, $(C_1$-$C_6)$-alkyl, $(C_1$-$C_6)$-alkoxy, $(C_6$-$C_{10})$-aryl, or $(C_5$-$C_{10})$-heteroaryl, or W is X—S—Y—C(O)—R, wherein n, X, Y and R are as defined above.

In one embodiment, W is hydroxy-substituted $(C_1$-$C_{10})$-alkyl or hydroxy-substituted $(C_2$-$C_{10})$-alkenyl. In another embodiment, W is hydroxy-substituted $(C_1$-$C_6)$-alkyl or hydroxy-substituted $(C_2$-$C_6)$-alkenyl. In another embodiment, W is $CH_2$—OH.

In one embodiment, the dimer has the following structure

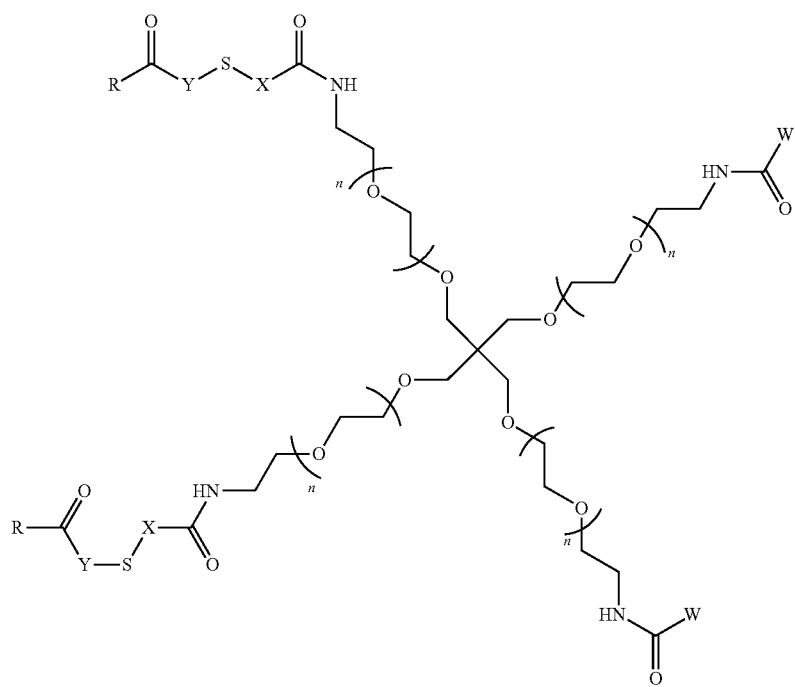

wherein W is independently or simultaneously hydroxy-substituted $(C_1-C_{20})$-alkyl or hydroxy-substituted $(C_2-C_{20})$-alkenyl, each of which is optionally substituted with one or more of halo, amino, hydroxy, $(C_1-C_6)$-alkyl, $(C_1-C_6)$-alkoxy, $(C_6-C_{10})$-aryl, or $(C_5-C_{10})$-heteroaryl, and n, X, Y and R are as defined above.

In another embodiment, the trimer has the following structure

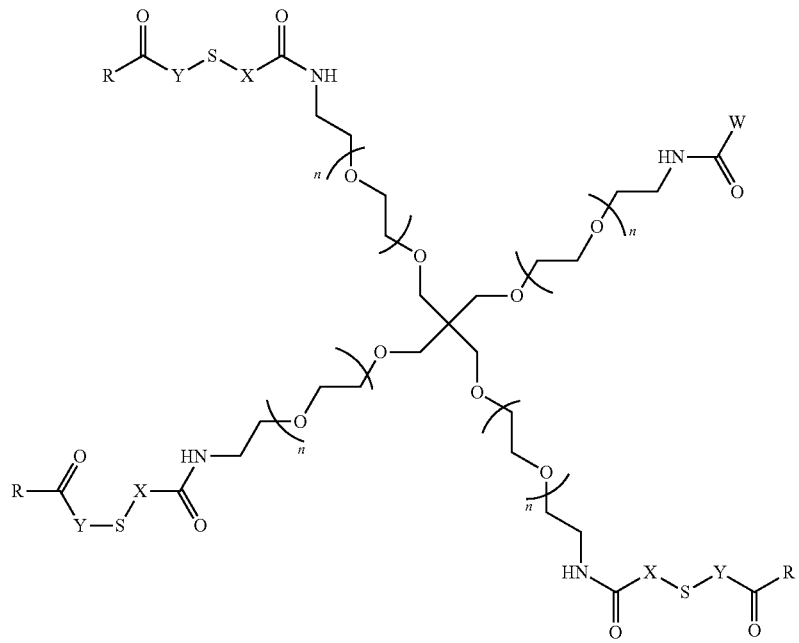

wherein W is independently or simultaneously hydroxy-substituted $(C_1-C_{20})$-alkyl or hydroxy-substituted $(C_2-C_{20})$-alkenyl, each of which is optionally substituted with one or more of halo, amino, hydroxy, $(C_1-C_6)$-alkyl, $(C_1-C_6)$-alkoxy, $(C_6-C_{10})$-aryl, or $(C_5-C_{10})$-heteroaryl, and n, X, Y and R are as defined above.

In another embodiment, the tetramers are the compounds of the formula (I).

In an embodiment, the compounds disclosed herein exhibit Tie 2 agonist activity. This Tie 2 agonist activity can be detected using indicators of Tie 2 activation that are well established in the art. For example, a compound disclosed herein can stimulate Tie 2 phosphorylation (e.g., phosphorylation at tyrosine residues, such as amino acid residue Y992 of human Tie 2).

Accordingly, in an embodiment, the compound stimulates Tie 2 phosphorylation.

Furthermore, a compound disclosed herein can stimulate phosphorylation of a molecule in a downstream signalling pathway of Tie 2, such as phosphorylation of MAPK, AKT (e.g., phosphorylation at amino acid residue S473 of human AKT) and/or eNOS (e.g., phosphorylation at amino acid residue S1177 of eNOS). The ability of a compound to stimulate phosphorylation of particular proteins can be determined using standard techniques well-known in the art, such as immunoblot assays of cell lysates treated with the compound.

Accordingly, in an embodiment, the compound stimulates phosphorylation of MAPK, AKT and eNOS.

In another embodiment, a compound disclosed herein has demonstrable effects on endothelial cells. For example, a compound disclosed herein may have at least one effect on endothelial cells selected from the group consisting of: stimulation of endothelial cell migration, stimulation of MMP2 release from endothelial cells and protection of endothelial cells from serum withdrawal-induced apoptosis. Optionally, a compound disclosed herein has at least two of these effects on endothelial cells or has all three of these effects on endothelial cells. The ability of a compound to have any of these effects on endothelial cells can be determined using assays known in the art, such as a Boyden chamber assay to assess cell migration, a zymography assay to assess MMP2 release or a cell death ELISA assay to assess serum withdrawal induced apoptosis.

Accordingly, in an embodiment, the compound stimulates endothelial cell migration; stimulates MMP2 release from endothelial cells and/or protection of endothelial cells from serum withdrawal-induced apoptosis.

In an embodiment, the compound disclosed herein has demonstrable effects on angiogenesis, as measured in an in vitro or in vivo angiogenesis assay. One such assay is an in vivo Matrigel assay, in which growth factor reduced Matrigel is impregnated with the compound and injected subcutaneously into a test animal. After a period of time (e.g., 14 days), the test animal can be treated with an agent that facilitates vessel identification and quantitation (e.g., FITC-lectin) and the Matrigel plug can be removed and examined for an angiogenic response.

Accordingly, in an embodiment, the compound disclosed herein stimulates an angiogenic response in vivo in a Matrigel assay.

In another embodiment, a compound disclosed herein can stimulate wound healing in a subject when applied topically to a wound of the subject. The ability of the compound to stimulate wound healing can be assessed in an animal model, such as the B6.Cg-m(+/+)Lepr(db)/J (db/db) strain of mouse, a diabetic strain of mouse that presents with impaired wound healing. An excisional wound can be made on the mouse, the compound, incorporated into a topical formulation, can be applied to the wound and wound healing can be assessed. In an embodiment, the compounds disclosed herein can accelerate wound closure times and/or can promote increases in collagen deposition and neovascularization.

Accordingly, in an embodiment, the compound stimulates wound healing in a subject when applied topically to a wound of the subject.

In one embodiment, the number of PEG molecules in the compound disclosed herein is optionally a number that results in a molecular weight of less than about 21,500 Daltons, in a molecular weight range of about 8,000 Daltons to about 21,500 Daltons, in a molecular weight of about 12,500 Daltons, about 15,500 Daltons, or about 14,000 Daltons.

Also provided herein is a pharmaceutical composition comprising a compound disclosed herein and a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Optionally, the carrier is suitable for topical administration or for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

Pharmaceutically acceptable carriers can be selected to be suitable for the desired route of administration. For example, in one embodiment, the pharmaceutically acceptable carrier is suitable for topical administration. A non-limiting example of a suitable carrier for topical administration is IntraSite Gel (commercially available from Smith & Nephew). In another embodiment, the pharmaceutically acceptable carrier is suitable for systemic administration. A non-limiting example of a suitable carrier for systemic (e.g., intravenous) administration is phosphate buffered saline (PBS).

In yet another embodiment, the pharmaceutically acceptable carrier is suitable for intranasal administration. In yet another embodiment, the pharmaceutically acceptable carrier is suitable for inhalation. In a further embodiment, the pharmaceutically acceptable carrier is suitable as a component of a perfusate.

The pharmaceutical compositions may include one or more pharmaceutically acceptable salts. A "pharmaceutically acceptable salt" refers to a salt that retains the desired biological activity of the original compound and does not impart any undesired toxicological effects (see e.g., Berge, S. M. et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like (such as acetic acid). Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain, for example, preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Therapeutic compositions typically must be sterile and stable under the conditions of manufacture and storage. Sterile injectable solutions can be prepared by incorporating the active compound in the required amount in an appropriate solvent with one or a combination of ingredients enumerated above, as required, followed by sterilization microfiltration. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions can be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

For systemic administration of the compound disclosed herein, the dosage typically ranges from about 0.00001 to 100 mg/kg, and more usually 0.1-100 µg/kg, of the host body weight. For example dosages can be 0.1 µg/kg, 0.5 µg/kg, 5 µg/kg, 10 µg/kg, 30 µg/kg, body weight, 0.1 mg/kg body weight, 0.3 mg/kg body weight, 0.5 mg/kg body weight or 1 mg/kg body weight. For topical administration, exemplary dosage concentrations are from about 1 ng/ml to about 10 ng/ml.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. One of ordinary skill in the art would be able to determine such amounts based on such factors as the subject's size, the severity of the subject's symptoms, and the particular composition or route of administration selected.

Methods of Making

Also provided herein is a method of making the compound of formula (I) disclosed herein comprising (i) reacting a peptide which is T7 peptide (SEQ ID NO:1), a GA3 peptide (SEQ ID NO:2), a T4 peptide (SEQ ID NO:3), a T6 peptide (SEQ ID NO:4) and/or a T8 peptide (SEQ ID NO:5) or a retro-inverso peptide thereof, with a thiol compound of the formula (II)

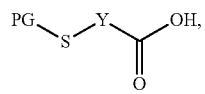

to obtain a compound of the formula (III) or a salt thereof

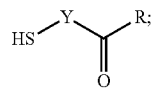

(ii) reacting the compound of the formula (III) with a PEG-tetramer of the formula (IV)

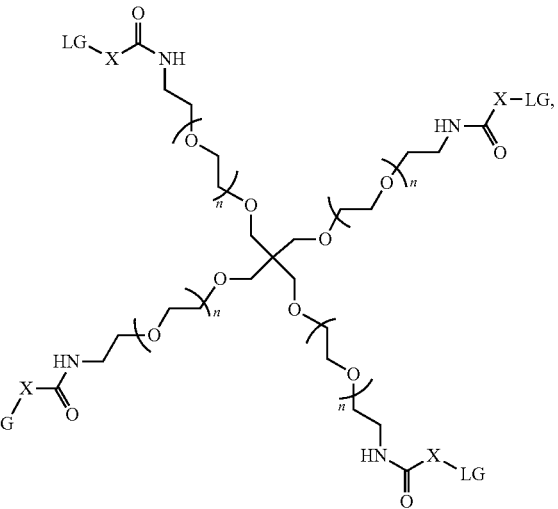

to obtain a compound of the formula (I), or pharmaceutically acceptable salt thereof;

wherein the variables n, X and Y are as defined above, LG is a suitable leaving group and PG is H or a suitable protecting group.

In one embodiment, the suitable leaving group is halo, a tosylate or a mesylate. In a further embodiment, the leaving group is bromo.

In one embodiment, the suitable protecting group is trityl.

In one embodiment, the compound of the formula (III) is an acid addition salt, such as a trifluoroacetate salt, acetate salt or hydrochloride salt.

In some embodiments, the peptide (R) is first bonded to a polystyrene resin. In another embodiment, the peptide bonded to the polystyrene resin is then reacted with a thiol compound of the formula (II). In a further embodiment, the compound of the formula (III) is bonded to a polystyrene resin, which is cleaved before being reacted with a compound of the formula (IV).

In one embodiment, the reaction between the compound of the formula (III) and the compound of the formula (IV) is conducted at a pH between about 5 to about 8, or about 6 to about 8, or about 6 to about 7, or 6.5.

In other embodiments, thiol compounds of the formula (III) are used as a nucleophile in a Michael addition reaction with tetrameric PEG molecules as described above and further containing unsaturated moieties. For example, compounds of the formula (III) are reacted with tetrameric PEG molecules such as

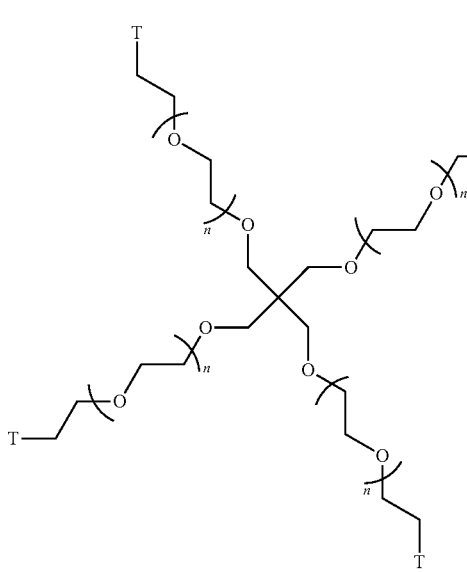
wherein
T is an unsaturated moiety such as an acrylate moiety, or a vinyl sulfone moiety.
In another embodiment, the acrylate moiety is
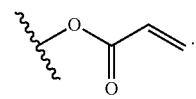
In another embodiment, the vinyl sulfone moiety is
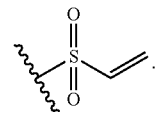
In one embodiment, the thiol moiety in the compound of the formula (III) acts as a nucleophile in a Michael addition reaction to form additional compounds of the disclosure, such as
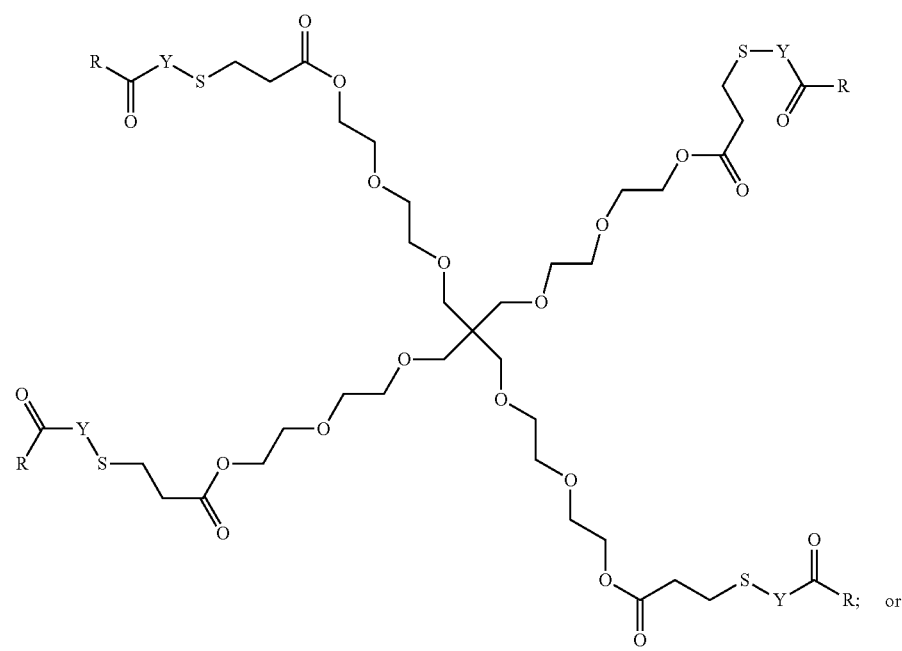

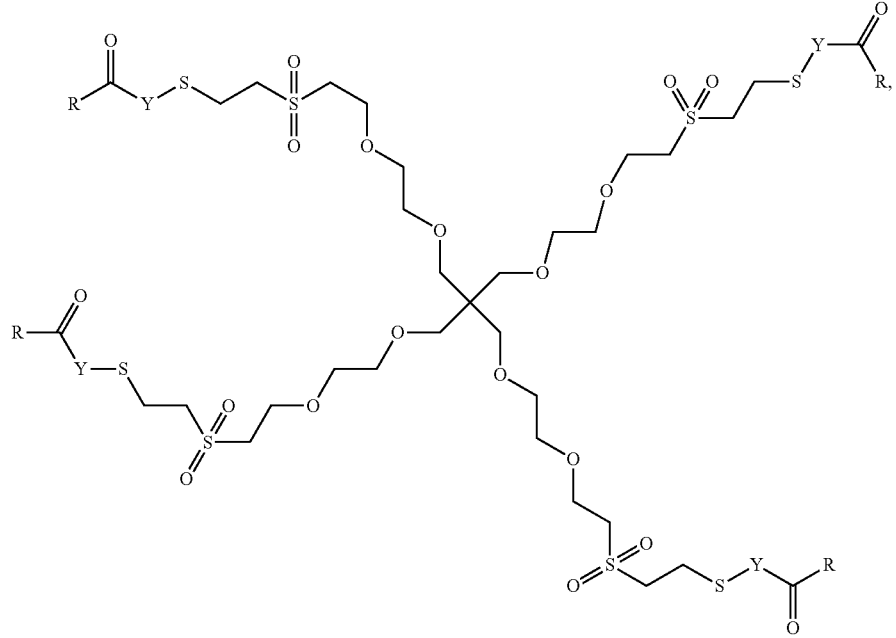

wherein R and Y are as defined above.

Methods and Uses

Tie2 Activation and Stimulation of Angiogenesis

Another aspect pertains to methods of using and uses of the compounds disclosed herein. As discussed herein, the compounds disclosed herein can be used to activate the Tie 2 receptor, either in vitro or in vivo. Thus, in an embodiment, there is provided a method of activating a Tie 2 receptor comprising contacting the Tie 2 receptor with the compound disclosed herein such that the Tie 2 receptor is activated. Also provided is use of a compound disclosed herein to activate a Tie 2 receptor. Further provided is use of a compound disclosed herein in the preparation of a medicament to activate a Tie 2 receptor. Even further provided is a compound disclosed herein for use in activating a Tie 2 receptor.

Activation of the Tie 2 receptor can be evidenced by any of numerous possible indicators of Tie 2 activation well established in the art, including but not limited to the various in vitro and in vivo assays. In one embodiment, for example, activation of the Tie 2 receptor is evidenced by phosphorylation of tyrosine residues of the Tie 2 receptor, for example, tyrosine 992 (Y992) of human Tie 2. In another embodiment, for example, activation of the Tie 2 receptor is evidenced by phosphorylation of MAPK, AKT or eNOS.

Since the compounds disclosed herein have been shown to have an increased magnitude of response and a broader dose range than vasculotide, which has been shown to have angiogenic activity (see, for example, FIGS. 3A,B, 4A,B, 5A-C and 8A), also provided is a method of stimulating angiogenesis in a subject comprising administering the compound disclosed herein to the subject in need thereof. Also provided is use of a compound disclosed herein for stimulating angiogenesis in a subject in need thereof. Further provided is use of a compound disclosed herein in the preparation of a medicament for stimulating angiogenesis in a subject in need thereof. Even further provided is a compound disclosed herein for use in stimulating angiogenesis in a subject in need thereof.

In an embodiment, angiogenesis stimulated by the compound is characterized by at least one of the following properties:
a) recruitment of perivascular support cells;
b) non-leakiness of vessels that would otherwise be leaky;
c) well-defined arborization; and
d) inhibition of endothelial cell apoptosis.

Recruitment of perivascular support cells can be demonstrated by detection of a marker of smooth muscle cells, for example by immunostaining with an antibody against smooth muscle actin 1 (Sma 1), NG2 or desmin. Non-leakiness of vessels can be assessed using vessel permeability assays established in the art, including in vitro and/or in vivo assays. A non-limiting example of an in vivo vessel permeability assay is the Miles assay using either Evan's Blue or FITC albumin. As used herein, vessels are to be considered "non-leaky" if the degree of permeability of the vessels is less than the degree of permeability of vessels whose growth was stimulated by VEGF treatment or treatment with other vascular inflammatory mediators, such as serotonin or histamine. Well-defined arborization can be demonstrated, for example, by imaging of newly formed vessels and quantification of number of vessels and number of nodes in a particular image field. Well-defined arborization is indicated by, for example, significant and organized branching of the vessels, such as angiogenesis in which the ratio of the number of vessels to the number of nodes is 1.0:0.5, optionally 1.0:0.7 or even 1.0:1.0. Furthermore, the flow dynamics of neovessels can be assessed using micro Doppler ultrasound.

In the method for stimulating angiogenesis, the site can be contacted with a compound disclosed herein alone or, alternatively, the site can be contacted with one or more additional angiogenic agents. Thus, in another embodiment, the angiogenesis method further comprises contacting the site in the subject with a second angiogenic agent. Non-limiting examples of additional angiogenic agents that can be used in combination with a compound disclosed herein include VEGF, PDGF, G-CSF, recombinant human erythropoietin, bFGF and placental growth factor (PLGF). Accordingly, in one embodiment, the second angiogenic agent is VEGF. In another embodiment, the second angiogenic agent is selected from the group consisting of PDGF, G-CSF, recombinant human erythropoietin, bFGF, Ang2 inhibitor, and placental growth factor (PLGF).

Given the ability of the compounds disclosed herein to stimulate angiogenesis, the compounds disclosed herein can be used in a variety of clinical situations in which promotion of angiogenesis is desirable. Non-limiting examples of such indications include vascularization of regenerative tissues, ischemic limb disease, cerebral ischemia, conditions of vascular inflammation including arteriosclerosis, avascular necrosis, stimulation of hair growth and erectile dysfunction.

Also provided herein is a method of decreasing vascular permeability at a site of leaky vessels comprising administering the compound disclosed herein to the site in a subject in need thereof. Also provided is use of a compound disclosed herein for decreasing vascular permeability at a site of leaky vessels in a subject in need thereof. Further provided is use of a compound disclosed herein in the preparation of a medicament for decreasing vascular permeability at a site of leaky vessels in a subject in need thereof. Even further provided is a compound disclosed herein for use in decreasing vascular permeability at a site of leaky vessels in a subject in need thereof.

In an embodiment, the subject has or had a stroke, macular degeneration, macular edema, lymph edema, breakdown of the blood-retinal barrier, breakdown of the blood-brain barrier, bacterial induced vascular leak, or requires normalization of tumor vasculature.

Vasculotide has previously been shown to have a protective effect on endothelial cells, e.g., by inhibiting apoptosis of endothelial cells. The ability of a Tie 2 agonist to protect endothelial cells in renal vasculature has been reported to ameliorate renal fibrosis in an experimental model (Kim, W. et al. (2006) *J. Am. Soc. Nephrol.* 17:2474-2483). MPA-Br has herein been shown to induce Tie2 phosphorylation in HUVECs, HMVECs and in primary rat, canine and cynomolgus monkey endothelial cells. VT was more recently shown by Thamm K et al 2016 to ameliorate acute kidney injury following transplant (in mice). This also translated into reduced transplant associated kidney fibrosis in those mice receiving VT. Rubig E et al, 2016 showed that VT reduced the extent of acute kidney injury following ischemia-reperfusion. Reduction in injury was marked by increased survival, improved blood flow within injured kidneys and reduced vascular leak.

Accordingly, provided herein is a method of protecting endothelial cells comprising administering a compound disclosed herein to a subject in need thereof. Also provided is a use of a compound disclosed herein for protecting endothelial cells in a subject in need thereof. Further provided is use of a compound disclosed herein in the preparation of a medicament for protecting endothelial cells in a subject in need thereof. Even further provided is a compound disclosed herein for protecting endothelial cells in a subject in need thereof.

Such a method or use can be used in a variety of clinical situations, non-limiting examples of which include lung injury, kidney injury, kidney fibrosis, stroke, vascular dementia, macular degeneration and diabetic complications (e.g., in the kidney, eye, skin and/or limbs).

Even further provided is a method of stimulating healing of a wound comprising administering a compound disclosed herein to a wound in a subject in need thereof. Also provided is a use of a compound disclosed herein for stimulating healing of a wound in a subject in need thereof. Further provided is use of a compound disclosed herein in the preparation of a medicament for stimulating healing of a wound in a subject in need thereof. Even further provided is a compound disclosed herein for use in stimulating healing of a wound in a subject in need thereof.

Stimulation of wound healing can be evidenced by, for example, accelerated wound closure time as compared to wound healing in the absence of the compound, increased granulation tissue at the wound site as compared to no treatment and/or enhanced neovascularization of the wound as compared to no treatment.

In one embodiment, the method or use of stimulating healing of wound is used in the treatment of a diabetic ulcer.

In other embodiments, the method or use for stimulating healing of a wound can be used in a variety of clinical situations involving wounds, including but not limited to decubitus ulcers, pressure ulcers, surgical incisions, traumatic tissue injuries, burns and skin grafts.

Conditions Associated with Eosinophils and/or Basophils

MPA-Br is a compound with improved target binding and pharmacokinetics over Vasculotide, which has been previously shown to inhibit the expansion of CFU-G cells.

Accordingly, provided herein is a method of inhibiting the expansion of CFU-G cells comprising administering the compound disclosed herein to a subject in need thereof. The disclosure also provides use of a compound disclosed herein for inhibiting the expansion of CFU-G cells in an animal or cell in need thereof. Also provided is use of a compound disclosed herein in the preparation of a medicament for inhibiting the expansion of CFU-G cells in an animal or cell in need thereof. Further provided is a compound disclosed herein for use in inhibiting the expansion of CFU-G cells in an animal or cell in need thereof.

The term "CFU-G" as used herein refers to colony-forming unit-granulocyte cells, which is a type of blood-forming cell that produces granulocytes, such as eosinophils, basophils and neutrophils. "Inhibition of expansion" as used herein refers to a decrease of at least 5%, 10%, 20%, 30%, 40%, 50%, 60%, 70%, 80% or more in the number of granulocyte colony-forming cells as compared to an untreated control.

MPA-Br is a compound with improved binding and pharmacokinetics over Vasculotide, which has previously been shown to result in a reduction in atopic disease, in circulating eosinophils and basophils, without a more general immunosuppression of T cells, B cells, monocytes or neutrophils. Accordingly, the present disclosure also provides a method of reducing eosinophils and/or basophils in an animal or cell in need thereof comprising administering a compound disclosed herein. The disclosure also provides use of a compound disclosed herein for reducing eosinophils and/or basophils in an animal or cell in need thereof. Also provided is use of a compound disclosed herein in the preparation of a medicament for reducing eosinophils and/or basophils in an animal or cell in need thereof. Further provided is a compound disclosed herein for use in reducing eosinophils and/or basophils in an animal or cell in need thereof.

The phrase "reducing eosinophils and/or basophils" as used herein refers to a reduction in the number of circulating eosinophils and/or basophils wherein at least 5%, 10%, 20%, 30%, 40%, 50%, 60%, 70%, or 80% less eosinophils and/or basophils are circulating compared to control. Further, reduction of basophils leads to reduction of mast cells, thus reduction of basophils, includes reduction of mast cells.

Eosinophils and basophils are implicated in the allergic response. Further, MPA-Br has been shown herein to attenuate vascular leak following cutaneous histamine exposure.

Accordingly, the present disclosure also provides a method of treating an allergic disease or response in an animal or cell in need thereof comprising administering a compound disclosed herein. The disclosure also provides use of a compound disclosed herein for treating an allergic disease or response in an animal or cell in need thereof. Also provided is use of a compound disclosed herein in the preparation of a medicament for treating an allergic disease or response in an animal or cell in need thereof. Further provided is a compound disclosed herein for use in treating an allergic disease or response in an animal or cell in need thereof.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

In an embodiment, the allergic disease or response is atopic disease. The term "atopic disease" as used herein refers to an allergic sensitivity affecting parts of the body not in direct contact with an allergen and is defined by an increase in levels of IgE in the serum of the animal. In one embodiment, the atopic disease is atopic dermatitis/eczema, asthma, conjunctivitis, chronic sinusitis, eosinophil esophagitis, food allergies or allergic rhinitis/hay fever. Asthma, allergic rhinitis and atopic dermatitis are commonly referred to as the atopic triad wherein in many cases atopic dermatitis is the first to manifest itself (Eichenfield et al. 2003) and is commonly followed by either the development of asthma and/or allergic rhinitis. Accordingly, in one embodiment, the atopic disease is atopic dermatitis. In another embodiment, the atopic disease is asthma.

In another embodiment, the present disclosure also provides a method of treating a condition associated with eosinophils and/or basophils in an animal or cell in need thereof comprising administering a compound disclosed herein. The disclosure also provides use of a compound disclosed herein for treating a condition associated with eosinophils and/or basophils in an animal or cell in need thereof. Also provided is use of a compound disclosed herein in the preparation of a medicament for treating a condition associated with eosinophils and/or basophils in an animal or cell in need thereof. Further provided is a compound disclosed herein for use in treating a condition associated with eosinophils and/or basophils in an animal or cell in need thereof. In one embodiment, the condition associated with eosinophils and/or basophils is a myelodysplastic syndrome. In another embodiment, the condition associated with eosinophils and/or basophils is a leukemia of eosinophil and/or basophil origin such as chronic myeloid leukemia, acute myeloid leukemia, chronic eosinophilc leukemia, acute eosinophilic leukemia, chronic myelomonocytic leukemia with eosinophilia, and acute basophilic leukemia. In another embodiment, the condition associated with eosinophils and/or basophils is inflammatory bowel disease. In yet another embodiment, the condition associated with eosinophils and/or basophils is a parasitic infection. In yet another embodiment, the condition associated with eosinophils and/or basophils is idiopathic hypereosinophilic syndrome (HES).

The present disclosure also provides a method of reducing inflammatory cytokine and/or chemokine levels in an animal or cell in need thereof comprising administering a compound disclosed herein. The disclosure also provides use of a compound disclosed herein for reducing inflammatory cytokine and/or chemokine levels in an animal or cell in need thereof. Also provided is use of a compound disclosed herein in the preparation of a medicament for reducing inflammatory cytokine and/or chemokine levels in an animal or cell in need thereof. Further provided is a compound disclosed herein for use in reducing inflammatory cytokine and/or chemokine levels in an animal or cell in need thereof. In one embodiment, the inflammatory cytokine and/or chemokine levels are serum inflammatory cytokine and/or chemokine levels. In one embodiment, the inflammatory cytokines and/or chemokines comprise at least one of eotaxin, IL-17, MIG, IL12/IL23 (p40), IL-9, MIP-1a, MIP-1b, RANTES, TNF-α, IL-1β, IL-5, IL-13, and MCP-1. In another embodiment, the inflammatory cytokines and chemokines comprise IL-17, MIG, IL12/IL23 (p40), IL-9, MIP-1a, MIP-1b, RANTES, TNF-α, IL-1β, IL-5, IL-13, and MCP-1. In yet another embodiment, the inflammatory cytokines and/or chemokines comprise eotaxin. Such methods and uses have therapeutic applications in treating diseases and conditions associated with increased inflammatory cytokines and/or chemokines.

In an embodiment, the methods and uses further comprise administration or use of an immunomodulator or corticosteroid in combination with the compound disclosed herein.

Influenza

MPA-Br, like Vasculotide, has been shown to improve morbidity and mortality in a mouse model of influenza but is effective at a lower dosage.

Accordingly, provided herein is a method of treating a subject infected with influenza comprising administering a compound disclosed herein to the subject in need thereof. Also provided is use of a compound disclosed herein for treating a subject infected with influenza. Further provided is use of a compound disclosed herein in the preparation of a medicament for treating a subject infected with influenza. Even further provided is a compound disclosed here for use in treating a subject infected with influenza.

The present disclosure also provides a method of decreasing lung endothelial leak in an animal or cell infected with influenza comprising administering a compound disclosed herein. The disclosure also provides use of a compound disclosed herein for decreasing endothelial leak in an animal or cell infected with influenza. Also provided is use of a compound disclosed herein in the preparation of a medicament for decreasing endothelial leak in an animal or cell infected with influenza. Further provided is a compound disclosed herein for use in decreasing endothelial leak in an animal or cell infected with influenza.

As used herein, the term "influenza" refers to an infectious disease caused by RNA viruses of the family Orthomyxoviridae. The term influenza also refers to primary viral pneumonia. In one embodiment, influenza is a disease caused by a human influenza virus. Human influenza viruses can be distinguished from avian influenza viruses (for example, H5N1 avian influenza) by the lack of certain basic amino acids in their hemagglutinin molecules; this limits cleavage to trypsin-like proteases that are contained within the respiratory tract. Thus, human influenza primarily infects the respiratory epithelium leading to epithelial injury, apoptosis and desquamation (Kuiken and Taubenberger, 2008). In contrast, avian influenza viruses can replicate outside of the respiratory tract and target endothelial cells. Human influenza viruses can also be distinguished from avian influenza viruses on the basis that human influenza viruses can spread from human to human but avian influenza viruses cannot spread from human to human. Non-limiting examples of human influenza viruses include the following: H1N1, H3N2, H2N2, and H1N2.

As used herein, the term "lung endothelial leak" refers to a loss of barrier integrity or increased permeability of the lung microvascular endothelium. The term "decreasing lung endothelial leak" refers to a decrease of lung endothelial leak of at least 5, 10, 15, 25, 50, 75 or 100% compared to a control that is not treated by the methods and uses described herein. In one embodiment, lung endothelial leak is measured by transendothelial electrical resistance (TEER) or fluorescence of a fluorescein-tagged compound such as dextran. The term "decreasing lung endothelial leak" also refers to an increase in permeability of lung microvascular endothelium of at least 5, 10, 15, 25, 50, 75 or 100% compared to a control that is not treated by the methods and uses described herein.

Low-dose infection with influenza predisposes the lung endothelium to increased leak upon subsequent exposure to bacteria, a phenomenon known as priming and it has been previously shown that Vasculotide is able to abrogate this priming-induced leak. MPA-Br which has improved binding of the Tie 2 receptor and lower dosage required in a mouse model of influenza is expected to provide similar or improved activity at the same or lower dosages.

Accordingly, the present disclosure also provides a method of treating a bacterial superinfection associated with influenza in an animal or cell in need thereof comprising administering a compound disclosed herein. The disclosure also provides use of a compound disclosed herein for treating a bacterial superinfection associated with influenza in an animal or cell in need thereof. Also provided is use of a compound disclosed herein in the preparation of a medicament for treating a bacterial superinfection associated with influenza in an animal or cell in need thereof. Further provided is a compound disclosed herein for use in treating a bacterial superinfection associated with influenza in an animal or cell in need thereof.

The present disclosure also provides a method of increasing survival and/or decreasing mortality in an animal or cell with a bacterial superinfection associated with influenza comprising administering a compound disclosed herein. The disclosure also provides use of a compound disclosed herein for increasing survival and/or decreasing mortality in an animal or cell with a bacterial superinfection associated with influenza. Also provided is use of a compound disclosed herein in the preparation of a medicament for increasing survival and/or decreasing mortality in an animal or cell with a bacterial superinfection associated with influenza. Further provided is a compound disclosed herein for use in increasing survival and/or decreasing mortality in an animal or cell with a bacterial superinfection associated with influenza.

The present disclosure also provides a method of decreasing lung endothelial leak in an animal or cell with a bacterial superinfection associated with influenza comprising administering a compound disclosed herein. The disclosure also provides use of a compound disclosed herein for decreasing lung endothelial leak in an animal or cell with a bacterial superinfection associated with influenza. Also provided is use of a compound disclosed herein in the preparation of a medicament for decreasing lung endothelial leak in an animal or cell with a bacterial superinfection associated with influenza. Further provided is a compound disclosed herein for use in decreasing lung endothelial leak in an animal or cell with a bacterial superinfection associated with influenza.

As used herein, the term "bacterial superinfection" refers to a bacterial infection that arises secondary to, or typically following, a primary influenza infection, including a low-dose influenza infection. A bacterial superinfection can also be defined as a pneumonia that occurs simultaneous with or following influenza infection. In one embodiment, the bacterium responsible for the bacterial superinfection is a Gram-positive bacterium such as *Staphylococcus aureus* (*S. aureus*) or *Staphylococcus* pneumonia (*S. pneumonia*). Without being bound by theory, it is believed that influenza primes the lung endothelium, making it more susceptible to leak when a secondary bacterial infection occurs. As a result, bacterial superinfections can cause severe lung injury after otherwise routine infections with influenza.

As used herein, the expression "a bacterial superinfection associated with influenza" refers in one embodiment to a bacterial superinfection that occurs at the same time, or simultaneously with, an influenza infection. In another embodiment, the expression "a bacterial superinfection associated with influenza" refers to a bacterial superinfection that occurs subsequent to, or following, an influenza infection.

Current treatment with antiviral agents is not as effective as time passes between initial onset of infection and treatment, which is problematic as patients do not always present for treatment immediately after symptoms arise. In contrast to the declining efficacy of antiviral treatment, Vasculotide was previously demonstrated to be effective even if given in a delayed fashion and MPA-Br also showed effectiveness when administration was delayed for 48 hours post infection.

Accordingly, in an embodiment, the compound disclosed herein is used or administered about or at least 24 hours post-infection. In another embodiment, the compound disclosed herein is used or administered about or at least 48 hours post-infection. In yet another embodiment, the compound disclosed herein is used or administered about or at least 72 hours post-infection.

Treatment with Vasculotide was also previously shown not to reduce the efficacy of antiviral treatment and to increase survival in a mouse model of primary viral pneumonia and acute lung injury due to influenza. It is expected that MPA-Br would have similar or improved activity at the same or lower dosages. Accordingly, the present disclosure also provides a method of treating an animal or cell infected with influenza comprising administering (a) a compound disclosed herein and (b) an antiviral agent to the animal or cell in need thereof. The disclosure also provides use of (a) a compound disclosed herein and (b) an antiviral agent for treating an animal or cell infected with influenza. Also provided is use of (a) a compound disclosed herein and (b) an antiviral agent in the preparation of a medicament for treating an animal or cell infected with influenza. Further provided is (a) a compound disclosed herein and (b) an antiviral agent for use in treating an animal or cell infected with influenza.

The present disclosure also provides a method of increasing survival and/or decreasing mortality in an animal or cell infected with influenza comprising administering (a) a compound disclosed herein and (b) an antiviral agent. The disclosure also provides use of (a) a compound disclosed herein and (b) an antiviral agent for increasing survival and/or decreasing mortality in an animal or cell infected with influenza. Also provided is use of (a) a compound disclosed herein and (b) an antiviral agent in the preparation of a medicament for increasing survival and/or decreasing mortality in an animal or cell infected with influenza. Further provided is (a) a compound disclosed herein and (b) an antiviral agent for use in increasing survival and/or decreasing mortality in an animal or cell infected with influenza.

The present disclosure also provides a method of decreasing lung endothelial leak in an animal or cell infected with influenza comprising administering (a) a compound disclosed herein and (b) an antiviral agent. The disclosure also provides use of (a) a compound disclosed herein and (b) an antiviral agent for decreasing lung endothelial leak in an animal or cell infected with influenza. Also provided is use of (a) a compound disclosed herein and (b) an antiviral agent in the preparation of a medicament for decreasing lung endothelial leak in an animal or cell infected with influenza. Further provided is (a) a compound disclosed herein and (b) an antiviral agent for use in decreasing lung endothelial leak in an animal or cell infected with influenza.

The term "antiviral agent" as used herein refers to a drug used to treat viral infections such as infections with influenza viruses. In one embodiment, an antiviral agent is an agent that suppresses the ability of a virus to reproduce. Examples of antiviral agents include, but are not limited to, amantadine, rimantadine, zanamivir, peramivir, viramidine, ribavirin and oseltamivir (also known as Tamiflu®).

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. As used herein, the term "treatment or treating" also includes preventing or retarding a bacterial superinfection secondary to viral infection with influenza. Examples of beneficial results of flu treatment include increasing survival, decreasing mortality, decreasing lung endothelial leak, decreasing weight loss and/or preventing hypothermia and improving arterial oxygenation.

The term "increasing survival" as used herein means increasing the length of time an animal survives following infection with influenza and/or bacterial superinfection associated with influenza. In one embodiment, the term "increasing survival" refers to at least a 5, 10, 25, 50, 75, 100, 200% increase in the length of time an animal survives following infection with influenza compared to an animal that is not treated with the methods and uses described herein.

The term "decreasing mortality" as used herein means decreasing the mortality rate of an animal or cell with influenza and/or bacterial superinfection associated with influenza when compared to an animal that is not treated with the methods and uses described herein. In one embodiment, the mortality rate is decreased by at least 5, 10, 15, 20, 25, 30, 35, 40, 45, 50, 55, 60, 65, 70, 75, 80, 85, 90, 95% when compared to an animal that is not treated with the methods and uses described herein.

The term "administering" includes the administration of the agents described herein to an animal or to a cell in vitro or in vivo.

The term "subject" or "animal" as used herein includes all members of the animal kingdom including humans.

The term "cell" includes a single cell as well as a plurality or population of cells. Administering to a cell includes administering in vitro (or ex vivo) as well as in vivo.

The compound disclosed herein may be administered by any suitable method, including topically, systemically, orally, intranasally or by inhalation.

The antiviral agent may also be administered in any suitable manner, including without limitation, topically, systemically, orally, intranasally or by inhalation.

The compound disclosed herein and the antiviral agent may be administered concurrently (at the same time). In another embodiment, the compound disclosed herein and the antiviral agent may be administered sequentially. The compound disclosed herein may be administered before the antiviral agent or the antiviral agent may be administered before the compound disclosed herein. In an embodiment, the compound disclosed herein is used or administered about or at least 24 hours after the anti-viral agent. In another embodiment, the compound disclosed herein is used or administered about or at least 48 hours after the anti-viral agent. In yet another embodiment, the compound disclosed herein is used or administered about or at least 72 hours after the anti-viral agent.

Administration of an "effective amount" of the agents described herein is defined as an amount effective, at dosages and for periods of time necessary to achieve the desired result. The effective amount of the compound disclosed herein may vary according to factors such as the disease state, age, sex, and weight of the animal. The effective amount of the antiviral agent may also vary according to factors such as the disease state, age, sex, and weight of the animal.

Dosage regimens may be adjusted to provide the optimum therapeutic response. For example, several divided doses may be administered daily or the dose may be proportionally reduced as indicated by the exigencies of the therapeutic situation. The mode of administration (e.g. in vivo by injection or topical application or ex vivo in culture) will also impact the dosage regime.

The methods and uses described herein include administration or use of compound disclosed herein alone or as part of a pharmaceutical composition comprising the compound disclosed herein.

In one embodiment, the pharmaceutical composition comprising the compound disclosed herein for use in the methods and uses herein further comprises an antiviral agent and/or a second angiogenic agent disclosed herein. Optionally, the composition further comprises a pharmaceutically acceptable carrier.

Such pharmaceutical compositions can be for intralesional, intravenous, topical, rectal, parenteral, local, inhalant, intranasal or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions. The composition can also be in the form of a perfusate.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003-20$^{th}$ Edition) and in The United States Pharmacopeia: The National Formulary (USP 24 NF19) published in 1999.

On this basis, the pharmaceutical compositions for use in the methods and/or uses described herein include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as corticosteroids and immune modulators.

Also provided is a composition comprising (a) a compound disclosed herein and (b) an antiviral agent and/or a second angiogenic agent disclosed herein. Optionally, the composition further comprises a pharmaceutically acceptable carrier.

Further provided is a kit comprising (a) a compound disclosed herein and (b) a second angiogenic agent disclosed herein. In one embodiment, the kit further comprises a container. In another embodiment, the kit contains instructions for use of the kit for stimulating angiogenesis in an animal or cell in need thereof and/or for carrying out methods and uses disclosed herein.

Further provided is a kit comprising (a) the compound disclosed herein and (b) an antiviral agent as described herein. In one embodiment, the kit further comprises a container. In another embodiment, the kit contains instructions for use of the kit for treating influenza in an animal or cell in need thereof and/or for increasing survival and/or decreasing mortality in an animal with influenza. In other embodiments, the kit contains instructions for use of the kit for treating a bacterial superinfection associated with influenza in an animal or cell in need thereof. In further embodiments, the kit provides instructions for use of the kit for decreasing lung endothelial leak in an animal with influenza.

The compound disclosed herein and the antiviral agent or second angiogenic agent of the kit are optionally for use concurrently or sequentially. The compound disclosed herein may be for use before the antiviral/second angiogenic agent or the antiviral/second angiogenic agent may be for use before the compound disclosed herein.

Biomaterials

The compounds disclosed herein can also be incorporated into a biomaterial that then can be implanted at a site in a subject to thereby provide the effects of the compound at that site. Biomaterials that provide a matrix or scaffold are suitable for use. The compound can be incorporated alone or in combination with one or more additional agents, such as VEGF, PDGF, G-CSF, recombinant human erythropoietin, bFGF and placental growth factor (PLGF). Non-limiting examples of suitable biomaterials include Matrigel, skin substitutes and cross-linked glycosaminoglycan hydrogels (e.g., as described in Riley, C. M. et al. (2006) *J. Biomaterials* 27:5935-5943). Accordingly, another aspect pertains to a biomaterial composition into which is incorporated a compound disclosed herein, alone or in combination with one or more additional agents. A packaged material that comprises the biomaterial is also encompassed. The packaged material can be labeled for use of the biomaterial.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Results

Detection of Parental Vasculotide and MPA-Br Binding to a Homogeneous, Species-Specific Recombinant Receptor Population Using Tryptophan Fluorescence Spectroscopy.

The amino acids tryptophan, tyrosine and phenylalanine display intrinsic fluorescence properties when excited at a wavelength of 280 nm, and specifically for tryptophan at 295 nm. This emission spectrum is highly dependent on the protein's structural conformation and its solvent. With regards to structural conformation, changes in the spectrum that occur due to the binding of a ligand to its receptor have been used as an intrinsic marker to characterize dose dependent binding. To this end, the intrinsic fluorescent properties of species-specific Tie2Fc proteins and the change in emission spectra when in the presence of parental Vasculotide or MPA-Br were utilized to characterize binding kinetics.

Figure 2A:
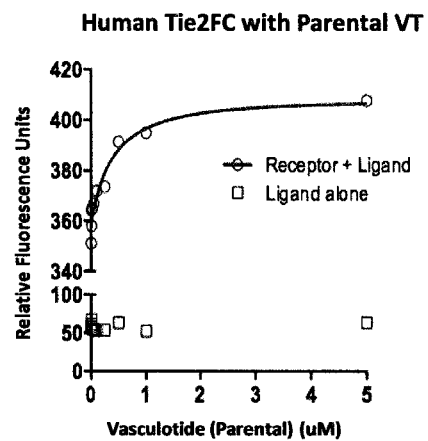
FIG. 2A shows detection of parental Vasculotide binding to a homogeneous recombinant receptor population, human Tie2Fc in solution using tryptophan fluorescence spectroscopy.
Figure 2B:
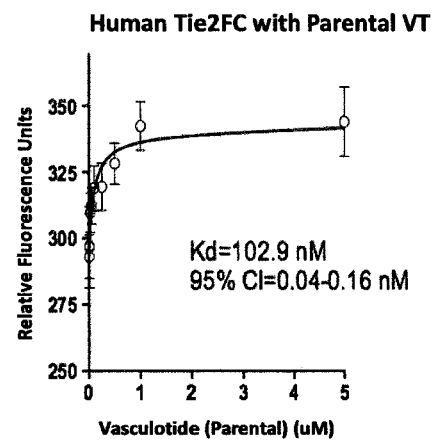
FIG. 2B shows specific saturation binding curves of parental Vasculotide to human Tie2Fc.
Figure 2C:
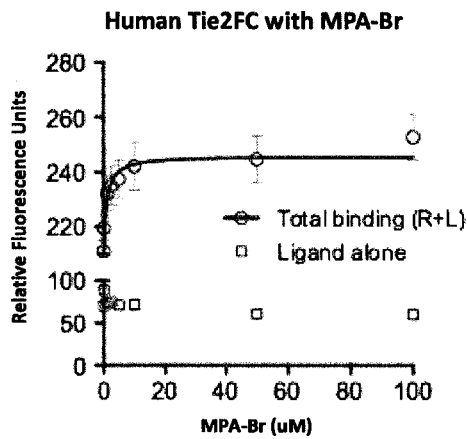
FIG. 2C shows detection of MPA-Br binding to a homogeneous recombinant receptor population, human Tie2Fc in solution using tryptophan fluorescence spectroscopy. An increase in intrinsic fluorescence intensity and the resulting binding curves upon incubation of human Tie2Fc receptor with increasing concentrations of the ligand (A,C) (○) or ligand alone (□). Samples were excited at a wavelength of 295 nm.
Figure 2D:
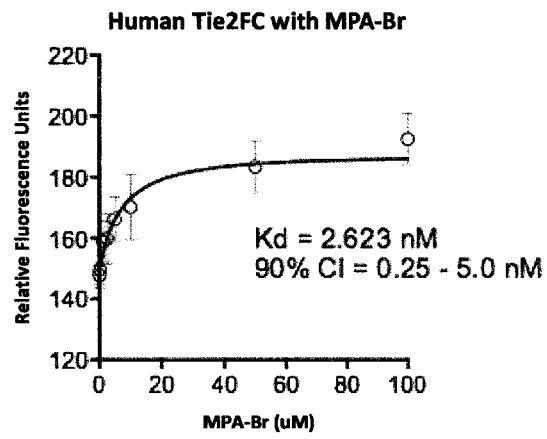
FIG. 2D shows specific saturation binding curves of Mpa-Br to human Tie2Fc. For non-linear regression one site specific binding, intrinsic fluorescence intensity of parental Vasculotide alone or MPABr alone was subtracted from total binding. The resulting Kd values for the normalized specific binding of parental Vasculotide and MPA-Br to human Tie2Fc are 102.9 nM and 2.623 nM respectively.

A dose dependent increase in intrinsic fluorescence intensity was observed with the incubation of recombinant human Tie2Fc receptor and the ligands parental Vasculotide or MPA-Br (FIG. 2A,C). In both cases, the fluorescence intensity was found to be saturable. The specific signal was derived by subtraction of the fluorescence intensity generated by ligand alone from the receptor and ligand complex. The resulting Kd for the normalized specific binding of parental Vasculotide and MPA-Br to human Tie2Fc is 102.9 nM and 2.623 nM, using non-linear regression one site specific binding (FIG. 2B,D). Identical studies were performed for parental Vasculotide and MPA-Br for recombinant mouse Tie2Fc and MPA-Br alone with recombinant rat and cynomolgus monkey Tie2Fc (raw data not shown). The determined dissociation constants (Kd) are detailed in FIG. 2G.

Given that the recombinant Tie2 receptor is a fusion protein with human IgG Fc, the ability of recombinant human IgG Fc to bind parental Vasculotide or MPA-Br was determined. Significantly, no dose dependent increase in fluorescence intensity was observed for either ligand (FIG. 2E,F).

Parental Vasculotide and MPA-Br Induce Tie2 and MAPK Phosphorylation in HUVEC.

Figure 3A:
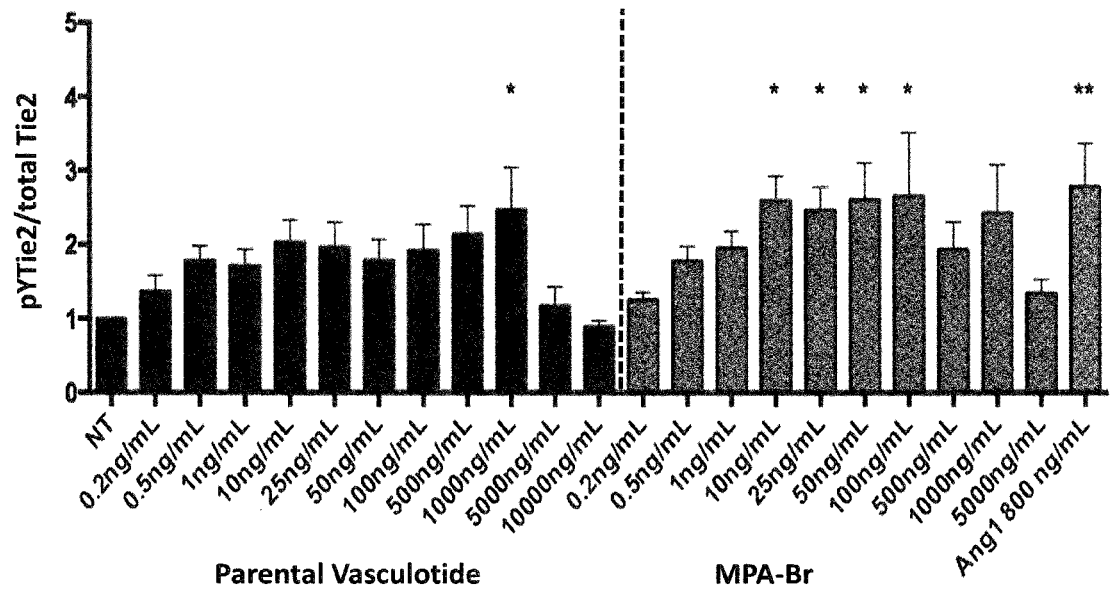
FIG. 3A shows parental Vasculotide and MPA-Br activate the Tie2 receptor. Phosphorylated Tie-2 in HUVEC cells treated with escalating doses of parental Vasculotide and MPA-Br. Data expressed as normalized mean±SEM, one-way ANOVA posthoc Holm-Sidak multiple comparisons relative to no treatment (NT), * $p<0.05$, ** $p<0.01$. For visual ease, the hatched line separates parental Vasculotide treatment from MPA-Br treatment.
Figure 3B:
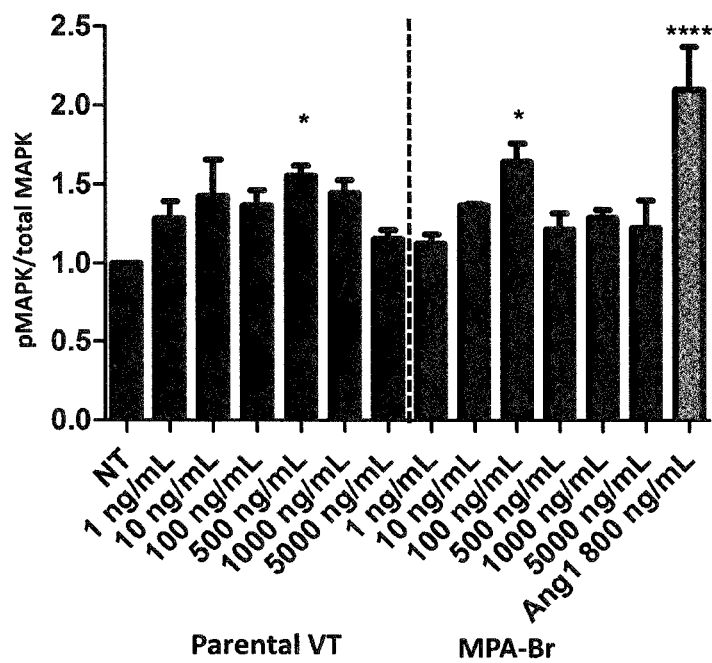
FIG. 3B shows parental Vasculotide and MPA-Br activate Mitogen Activated Protein Kinase (MAPK). Phosphorylation of MAPK (Erk2) in HUVEC cells treated with parental Vasculotide and MPA-Br. Data expressed as normalized mean±SEM, one-way ANOVA posthoc Holm-Sidak multiple comparisons relative to no treatment (NT), * $p<0.05$, **** $p<0.0001$.
Figure 4A:
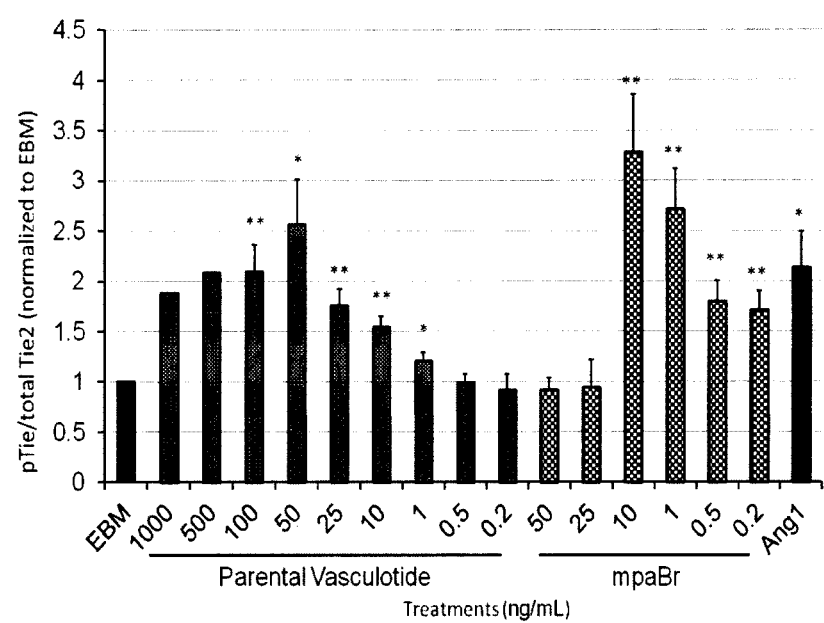
FIG. 4A shows phosphorylated Tie-2 in HMVEC$^{tert}$ cells (immortalized with telomerase) treated with parental Vasculotide and MPA-Br at indicated concentrations (Data expressed as Mean±SEM, student t's test, * $p<0.05$, ** $p<0.01$, treatment group vs endothelial basal media (EBM)-treated group).
Figure 4B:
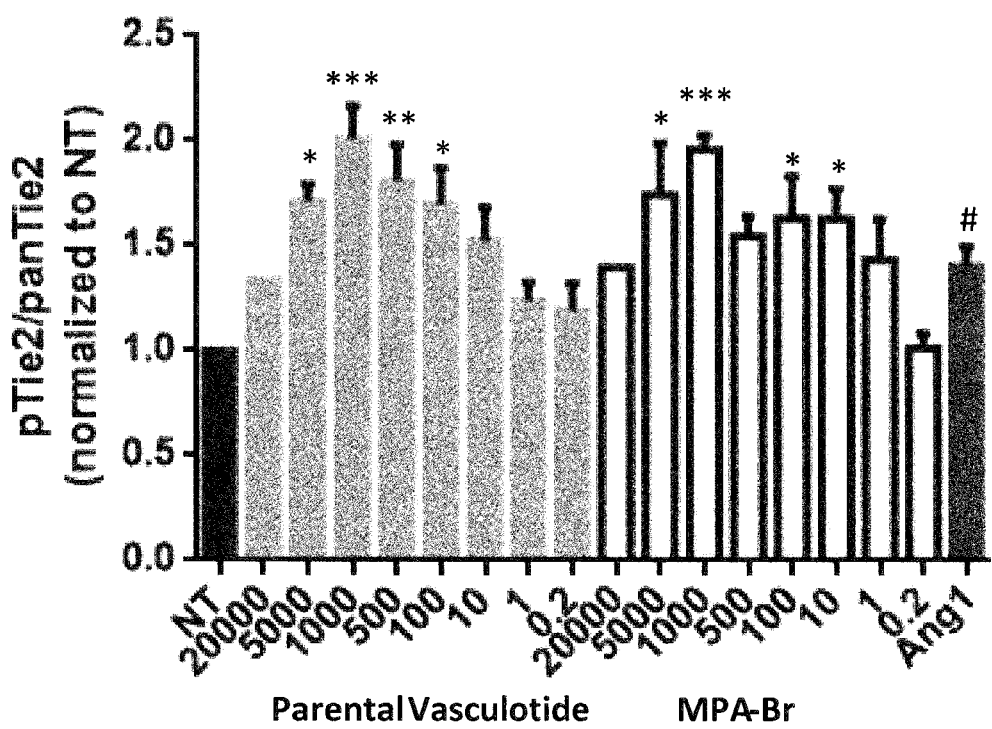
FIG. 4B shows phosphorylated Tie-2 in primary mouse lung microvascular endothelial cells treated with parental Vasculotide and MPA-Br at indicated concentrations (Data expressed as Mean±SEM, one way ANOVA posthoc Holm-Sidak, * $p<0.05$,  $p<0.01$, *$p<0.001$, #$p=0.06$ treatment group vs no treatment (NT).
Figure 5A:
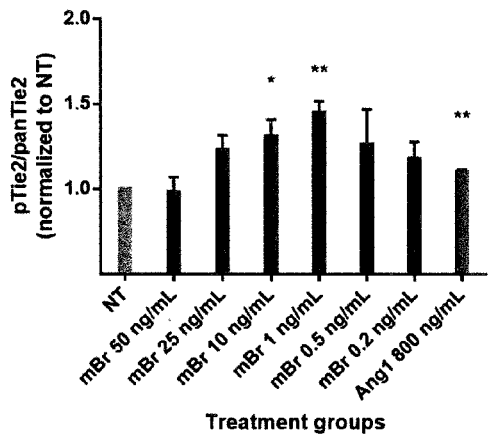
FIG. 5A shows primary cultured endothelial cells derived from rat glomeruli.
Figure 5B:
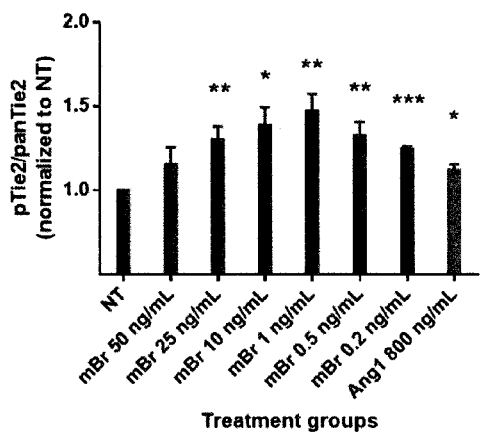
FIG. 5B shows primary cultured endothelial cells derived from canine aorta and FIG. 5C shows primary cultured endothelial cells derived from cynomolgus monkey glomeruli. The cells were stimulated with indicated concentrations of MPA-Br (mBr) for 15 minutes. Phosphorylated Tie2 was quantified via ELISA and data shown represent the relative activation of Tie2 (pTie2) when normalized to total Tie2 protein levels. Human recombinant angiopoietin 1 (Ang1) was included as a positive control. Data expressed as Mean±SEM, student t's test, * $p<0.05$,  $p<0.01$, *$p<0.001$ treatment group vs no treatment (NT). n=3 for rat, n=4 for canine and n=3 for cynomolgus.
Figure 5C:
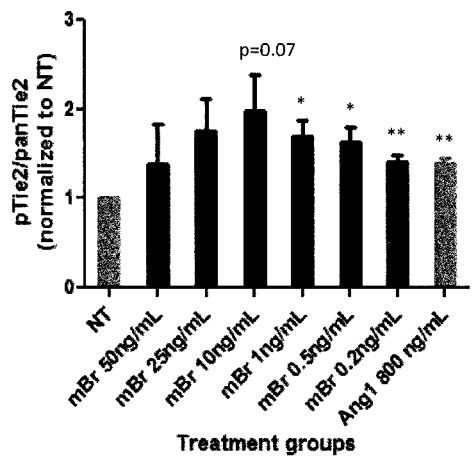

The Tie2 activation potential of parental Vasculotide and MPA-Br was evaluated in human umbilical vein endothelial cells (HUVEC). HUVECs treated with varying doses of both ligands displayed increases in activation of Tie2 and the downstream signaling molecule, MAPK (FIG. 3A,B). In general, MPA-Br displayed an increased magnitude of response and a broader dose range starting at lower concentrations than did parental Vasculotide; significantly activating Tie2 at doses from 10-100 ng, compared to only a single significant response at 1000 ng/ml for parental Vasculotide. Parental Vasculotide and MPA-Br treatment both displayed characteristic bell shaped dose response for the Tie2 receptor. This type of dose response has been previously noted for Tie2 ligands and seems to be a common feature associated with activating this receptor tyrosine kinase (Brkovic A, et al 2007, Sturn D H, et al 2005, Murdoch C, et al 2007, Gruber B L, et al 1995 and Maliba R, et al 2008). Stimulation of HUVECs with either parental Vasculotide or MPA-Br resulted in downstream activation of MAPK. Human recombinant Ang1 was used as a positive control for Tie2 and MAPK activation studies.

Parental Vasculotide and MPA-Br Induce Tie2 Phosphorylation in HMVEC$^{tert}$.

Tie2 activation studies similar to those detailed above for HUVECs were completed in human microvascular endothelial cells (dermal origin) immortalized with telomerase (HMVEC$^{tert}$). It is well accepted that endothelial cells from different vascular beds, or relative calibres of vessels behave differently and as such studies that utilized HMVEC$^{tert}$ facilitated a comparison in human endothelial cells of different origins. Stimulation of HMVEC$^{tert}$ with indicated concentrations of parental Vasculotide or MPA-Br resulted in a dose-dependent activation of the Tie2 receptor (FIG. 3A). Again, the dose response was bell-shaped, with MPA-Br displaying statistically significant agonistic activity at concentrations ranging from 0.2 ng/ml to 10 ng/ml. Activation following parental Vasculotide stimulation became apparent at five times higher concentration and ranged from 1 ng/ml to 100 ng/ml. The relative magnitude of Tie2 activation was greater for MPA-Br (~3.3-fold) when compared to either parental Vasculotide (~2.6-fold) or human recombinant Ang1 (800 ng/ml). The increased agonistic potency of MPA-Br when compared to parental Vasculotide in both HUVEC and HMVEC$^{tert}$ might be a function of improved binding properties displayed for the human Tie2 receptor (see FIG. 2G).

Parental Vasculotide and MPA-Br Induce Tie2 Phosphorylation in MLMVEC.

Several preclinical efficacy studies detailed herein utilize mice as a test species. As such, to specifically assess the Tie2 agonistic potency of parental Vasculotide and MPA-Br an in vitro cell culture system using primary mouse lung microvascular endothelial cells (MLMVEC) was used. Parental Vasculotide and MPA-Br displayed concentration-specific, bell-shaped dose responses. MPA-Br mediated activation of Tie2 was apparent at concentrations ranging from 10 ng/ml to 5000 ng/ml while parental Vasculotide promoted activation of Tie2 at concentrations which ranged from 100 ng/ml to 5000 ng/ml. Relative magnitudes of induction for the Tie2 receptor were not different for parental Vasculotide and MPA-Br, albeit statistically significant activation of Tie2 occurred at a 10-fold lower concentration for MPA-Br than was the case for parental Vasculotide.

Parental Vasculotide and MPA-Br Induce Tie2 Phosphorylation in Primary Rat, Canine and Cynomolgus Monkey Endothelial Cells Primary cell cultures of rat glomerular endothelial cells, canine aortic endothelial cells and cynomolgus glomerular endothelial cells were stimulated with varying concentrations of MPA-Br. In all cases these cell culture assays displayed MPA-Br-dependent increases in Tie2 activation. Dose response resembled the characteristic bell-shape noted for human and mouse endothelial cell studies, with statistically significant increases in Tie2 receptor phosphorylation centered between 0.2 ng/ml and 50 ng/ml. In all cases, human recombinant Ang1 provided a significant increase in baseline Tie2 phosphorylation (compared to no treatment (NT)).

Figure 6A:
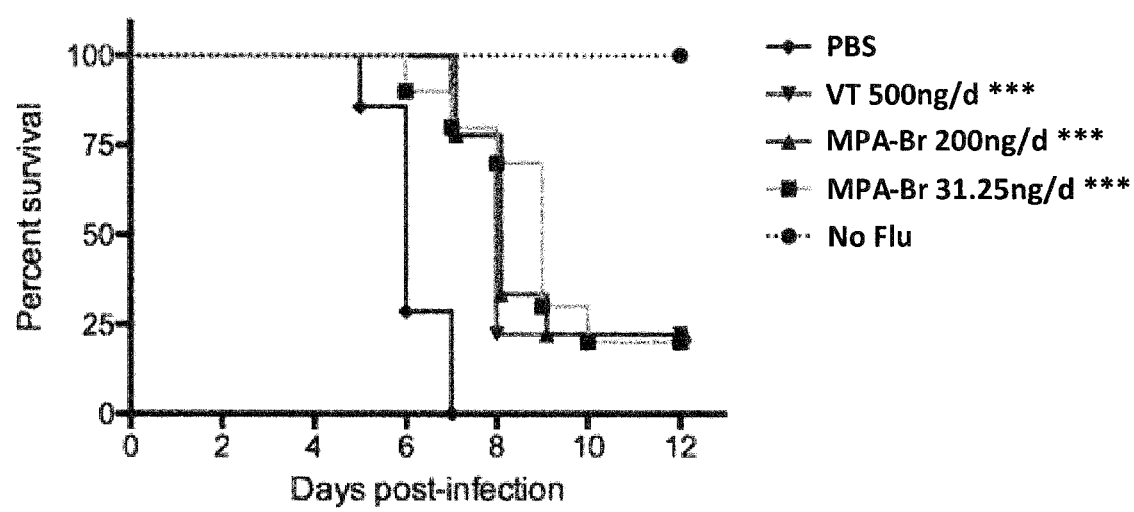
FIG. 6A-6I shows Parental VT and MPA-Br protect mice following inoculation with X31 (H3N2) influenza. Mice were intranasally infected with 64HAU X31 on day 0. Indicated doses of parental VT or MPA-Br were given intraperitoneally (I.P.) every 24 hrs starting at 48 hrs post infection for the duration of the study. Survival fraction was monitored daily (FIG. 6A) until day 12. Fraction of initial body weight measured 5 days (FIG. 6B) and 6 days (FIG. 6C) after infection. Arterial oxygen saturation on day 5 (FIG. 6D) and day 6 (FIG. 6E) after infection. Body temperature measured 5 days (FIG. 6F), or six days (FIG. 6G) after infection. Activity score measured at day 5 (FIG. 6H) and day 6 (FIG. 6I) following infection. Survival statistics were performed by Mantel Cox Log Rank analysis where ***$p<0.001$. All other statistical measures were as follows: #$p<0.05$ vs. Flu with PBS via 1-way ANOVA with Fisher's post hoc test, *$p<0.05$, $p<0.01$, *$p<0.001$ and ****p, 0.0001 vs Flu with PBS via 1-way ANOVA with Dunnett post hoc test.
Figure 6B:
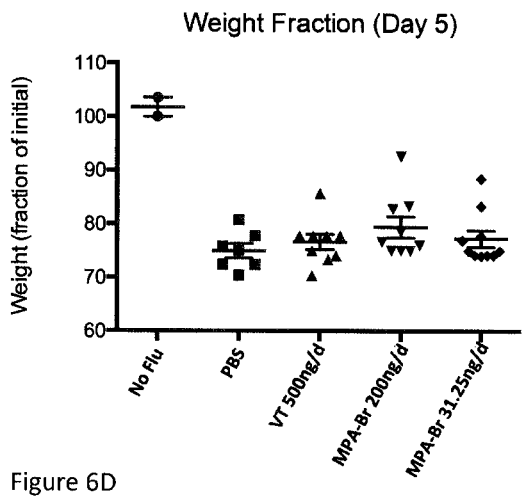
Figure 6C:
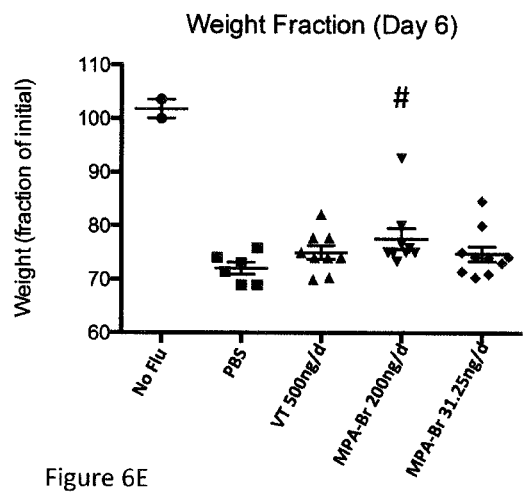
Figure 6D:
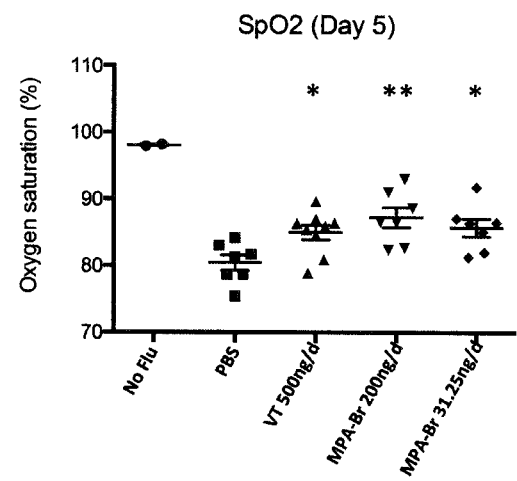
Figure 6E:
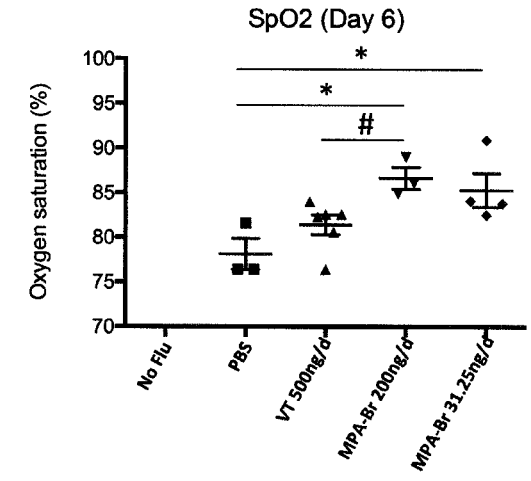
Figure 6F:
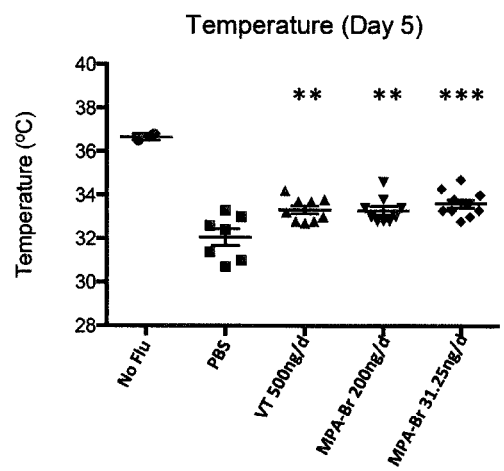
Figure 6G:
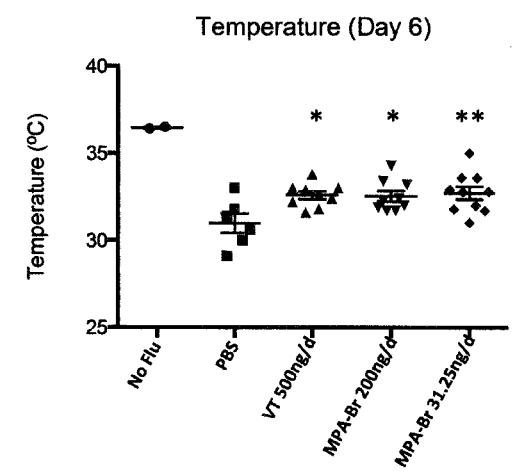
Figure 6H:
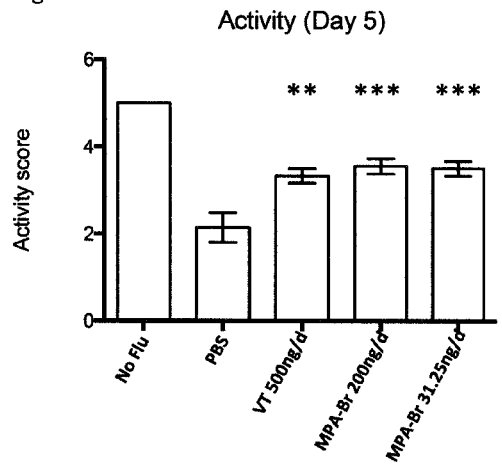
Figure 6I:
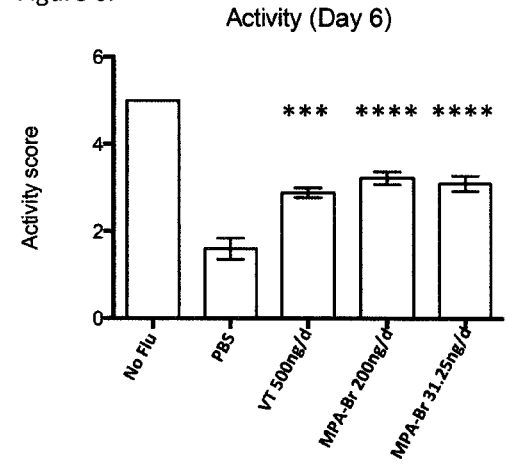

Parental Vasculotide and MPA-Br Improve Morbidity and Mortality Following Exposure to X31 (H3N2) Influenza C57Bl/6J mice infected with influenza (H3N2, 64HAU/mouse) developed weight loss (FIG. 6B,C) and began to succumb to lethal effects between 5-7 days after infection. The efficacy of parental Vasculotide administered at 100 ng/mouse/day was previously examined (Sugiyama M G et al, 2015) and found to be ineffective at enhancing survival following infection of C57Bl/6J mice with X31 influenza. Administration of parental Vasculotide (500 ng, intraperitoneally daily—previously defined to be optimal), or MPA-Br (31.25 ng or 200 ng, intraperitoneally daily) significantly improved overall survival of infected mice (p<0.001) (FIG. 6A). In addition, parental Vasculotide and MPA-Br significantly improved lung oxygenation (SpO2), thermal regulation, and activity score (FIG. 6 D-I). There were several measures where MPA-Br displayed superiority to parental Vasculotide. Those examples specifically include, protection from wasting (day 6, MPA-Br 200 ng/day, FIG. 6C) and arterial oxygenation (day 6, MPA-Br 200 ng/day, FIG. 6E). MPA-Br delivered at 31.25 ng/mouse/day represents a reduction in dose of 16-fold. In all study endpoints, MPA-Br delivered at 31.25 ng/mouse/day performed equal, or better than parental Vasculotide. This was also the case for MPA-Br 200 ng/mouse/day; representing a 2.5-fold reduction in dose compared to parental Vasculotide.

Figure 7A:
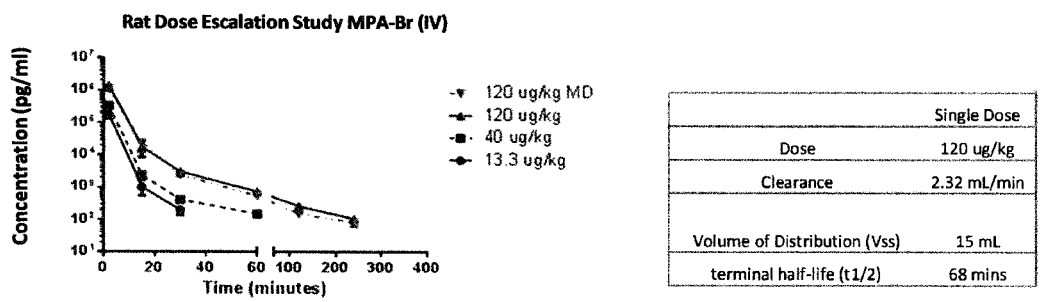
FIG. 7 A,B shows Sprague Dawley rats were given indicated doses of parental VT or MPA-Br via tail vein injection at time zero. Plasma was collected at indicated time points to facilitate quantification of circulating levels of test agent via ELISAs. Graphs depict the loss of circulating MPA-Br (FIG. 7A) and parental VT (FIG. 7B) from systemic circulation over time. Tables detail the calculated clearance, volume of distribution and terminal half life values for the 120 ug/kg dose. One arm of the study provided for MPA-Br to be delivered as a once every 24 hr dose for three consecutive days (multidose MD 120 ug/kg).
Figure 7B:
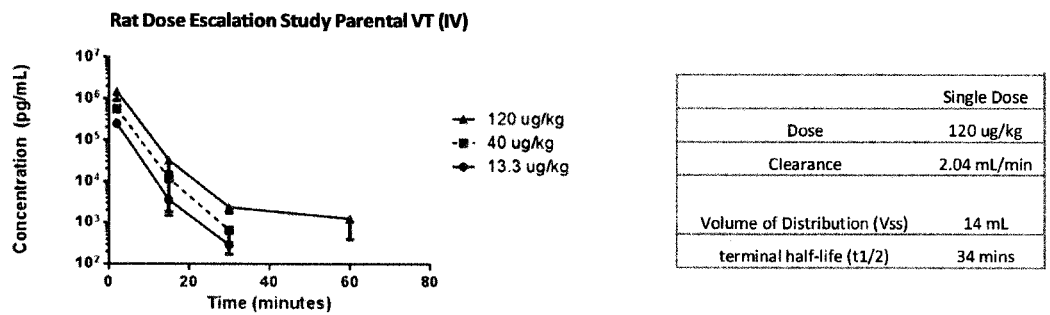

Pharmacokinetic Analysis of Parental Vasculotide and MPA-Br in Male Sprague Dawley Rats Indicated amounts (ug/kg) of parental Vasculotide and MPA-Br were intravenously administered via bolus injection to male Sprague Dawley rats. Serial, timed blood draws were performed and plasma preparations were applied to proprietary enzyme linked immunosorbent assays specifically designed to quantify parental Vasculotide or MPA-Br. Quantification of test agent over time facilitated calculation of pharmacokinetic (PK) measures including volume of distribution, clearance and terminal half life (FIG. 7A,B). The 120 ug/kg dose provided the greatest sensitivity of detection in these studies and as such, PK measures presented pertain to this particular dose level. Parental Vasculotide (FIG. 7B) and MPA-Br (FIG. 7A) displayed a similar volume of distribution and clearance rate, however MPA-Br circulated markedly longer than did parental Vasculotide ($t^{1/2}$ 68 min vs 34 min). MPA-Br PK was evaluated in a multi-dose (MD) intravenous setting at 120 ug/kg once every 24 hours for three consecutive days. This particular dosing approach did not differ from the single, 120 ug/kg IV dose, suggesting that there is no drug accumulation when administered daily.

Figure 8:
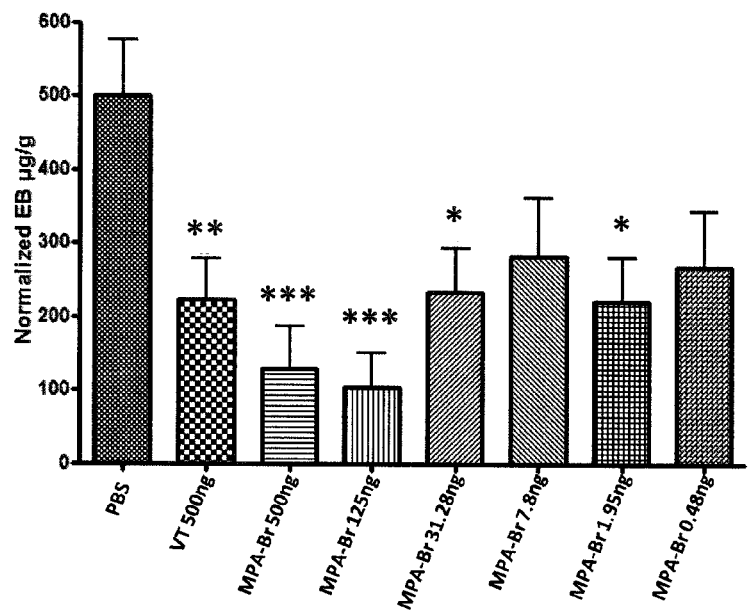
FIG. 8 shows male FVB mice with shaved dorsum were given indicated amounts of parental Vasculotide or MPA-Br (via IP) one hour prior to cutaneous histamine challenge. Evans blue (EB) dye, delivered via tail vein was administered immediately following histamine exposure. Standardized cutaneous skin biopsies were removed from cardiac perfused mice thirty minutes following the histamine challenge. Absorbance at 620 nm was used to calculate the quantity of EB dye extravassation for all treatment groups. Data expressed as mean quantity of EB±SEM, one-way ANOVA posthoc Dunnette's multiple comparisons relative to PBS vehicle control, * $p<0.05$,  $p<0.01$, * $p<0.001$.

Parental Vasculotide and MPA-Br Attenuate Vascular Leak Following Cutaneous Histamine Exposure Previous studies have highlighted the obligate role for Tie2 in opposing the induction of vascular leak following exposure to histamine. Specifically, mice that are genetically deficient in angiopoietin 2, a natural antagonist of Tie2, entirely fail to mount a vascular leakage response upon histamine challenge (Benest A V et al, Plos One, 2013). As such, administration of a specific agonist of Tie2, such parental Vasculotide and MPA-Br was hypothesized to inhibit histamine induced vascular leak. Male FVB mice that were given a prophylactic dose of parental Vasculotide or MPA-Br one hour prior to cutaneous histamine challenge displayed significantly less vascular leakage than vehicle treated mice; as assessed by extravassation of Evans blue dye tracer (FIG. 8A). Significantly, parental Vasculotide treatment delivered at an optimal dose of 500 ng/mouse performed less well at reducing histamine-induced vascular leakage than did MPA-Br at an equal dose, or 4-fold less (125 ng/mouse).

Methods and Materials:

Preparation of a Tetrameric Tie 2 Binding Peptide (T7) Via a 3-Mercaptopropionic Acid (Mpa) Linker Providing the Vasculotide Analog Mpa-Br.

Overview: The manufacturing process carried out for Mpa-Br required several steps. In the first stage the T7 peptide and the 3-mercaptoproprionic acid (Mpa) elaborated peptide was prepared using FMOC solid phase peptide synthesis techniques. This provided the Mpa-His-His-His-Arg-His-Ser-Phe-OH, which comprises the T7 peptide with a 3-mercaptopropionyl linker on the N-terminus (SEQ ID NO: 7). This was followed by cleavage and deprotection, RP-HPLC purification and freeze drying via lyophilization of the final product to isolate the Mpa-T7peptide as the TFA salt. In the second stage conjugation of the Mpa-peptide with (bromoacetimide)$_4$-PEG10K was executed followed by two levels of purification of the PEG conjugate. The first purification step includes RP-HPLC chromatography affording the Mpa-Br conjugate TFA salt. This product may be isolated at this stage via lyophilization, or the TFA counter ion directly exchanged to the acetate salt form via ion exchange chromatography without isolating the TFA salt intermediate. This initial product was freeze dried to isolate the Mpa-Br acetate as a free flowing solid.

Mpa T7-Peptide Manufacture

Step 1: On Resin Assembly

The T7 peptide sequence was assembled on Wang polystyrene resin (initial functionalization 1.2 mmol/g) with a 40 g resin input using a CS Bio peptide synthesizer. The Wang resin was loaded with Fmoc-Phe-OH using 8 eq of amino acid and 4 eq of DIC in DMF for 4 hours. An Fmoc loading test indicated that a 0.8 mmol/g loading was achieved corresponding to a 45.4 mmol scale synthesis. All amino acids were single coupled using DIC/Oxyma chemistry (3 eq, 136.2 mmol), 0.5M Ac$_2$O/DMF was used for capping and 20% piperidine/DMF for Fmoc deprotection. A trial cleave was carried out upon completion of the T7 peptide sequence and RP-HPLC analysis indicated that sequence had assembled successfully with 77.5% crude purity.

The coupling of Mpa, (Sigma-Aldrich, USA) to the resin bound T7 peptide was carried out using 3 eq Trt-Mpa-OH in the presence of 3 eq of DIC/Oxyma in DMF for 4 hours. After washing the resin (DMF, MeOH and MTBE) and drying overnight in a vacuum desiccator, 124.5 g of final resin was obtained (84.5 g weight gain) corresponding to a synthesis yield of 89.1%. A trial cleavage analysis indicated that the Mpa-T7 peptide had been formed with a crude purity of 78.5%. ESI-MS analysis confirmed that the Mpa peptide had been formed (MS observed=1044.4).

Step 2: Cleavage and Deprotection

The resin bound Mpa-T7 peptide was treated with a cleavage solution comprising TFA/TIS/water/EDT (92.5:2.5:2.5:2.5) for 3 hours. The peptide was precipitated with anti-solvent (iPr$_2$O) and the peptide was isolated by filtration to afford crude product. Resin bound Mpa-T7 peptide was cleaved to afford 31.5 g crude peptide, corresponding to an overall 38% recovery and 91.8% yield. RP-HPLC analysis of the crude product indicated that the crude purity was 70.5%.

Step 3: Purification

The crude Mpa-T7 peptide (24 g) was diluted in buffer A (15 mM TEAP) and purified using RP-HPLC on a Luna C18(3) PREP 250×50 mm Phenomenex column with a gradient of 5-10% buffer B (20% MeCN/water) and a flow rate of 88 mL/min. The product pool from the TEAP purification was combined and diluted 1 part in 5 with 0.5% TFA/water. Half of the peptide solution was loaded back onto the purification column and the product was initially washed on-column with eluted with water/MeCN (10%) containing 0.5% TFA before Buffer B was replaced with 0.1% TFA in MeCN and the product eluted by applying a gradient of 20-60% B. This step was repeated with the remaining peptide solution and the product pools combined and lyophilised to afford 11.4 g Mpa-T7 peptide as a TFA salt, corresponding to an overall 43.7% yield from the resin loading step. Final analysis indicated a peptide content of 61% and RP-HPLC purity of 96.2%, corresponding to 6.7 g net peptide (25.8% yield).

Mpa-Br Conjugate Manufacture

Step 1: Conjugation

The conjugation reaction was performed by dissolving Mpa-T7 peptide TFA salt (2 mmol) and (bromoacetimide)$_4$-PEG10K (JenKem, USA) (0.48 mmol) in 100 mM sodium phosphate (dibasic) buffer pH 8 containing 0.13M NaCl (120 ml). The pH of the reaction solution was confirmed to be pH 6.5 and the reaction mixture was stirred at 30° C. for 22 hours. The reaction progress was monitored by RP-HPLC and proceeded to approximately 58% conversion of the 4 arm substituted tetramer bromoacetimide to the fully conjugated product. At reaction completion the crude mixture contained on the order of ~30% of the 3-arm and ~7% 2-arm intermediates respectively. Small amounts of the single arm product was obtained.

Step 2: Purification of Mpa-Br TFA salt

The reaction mixture was diluted 1:1 with Buffer A (water+0.1% TFA) and purification was carried out collecting 10 mL fractions employing a Luna C18(3) PREP 250×30 mm column with a gradient of 10-75% Buffer B (MeCN:water (60:40)+0.1% TFA) and flow rate of 42 mL/min. The product isolated by lyophilisation at this stage provided the Mpa-Br TFA salt in a yield of about 45% and purity >99% by RP-HPLC.

Step 3: Mpa-Br Counter Ion Exchange

The Mpa-Br conjugate with TFA counter ion yields an amorphous material with a waxy/tacky consistency. In order to address the physical characteristics a salt exchange was performed directly from RP-HPLC purified Mpa-Br TFA salt fractions obtained as described in Step 2. Prior to lyophilization fractions were combined (~500 mL) and diluted 1:1 with water, the solution was loaded onto a RP-HPLC column and taken through the acetate exchange process using a Luna C18(3) PREP 250×30 mm column with a flow rate of 42 mL/min, collecting 10 mL fractions following several steps including; initial column equilibration 0.5M NH$_4$OAc containing 1% AcOH), loading sample followed by the exchange process (0.5M NH$_4$OAc containing 1% AcOH), ammonium acetate removal step (1% AcOH (Buffer A) and MeCN (Buffer B), 10% B) and the elution process (1% AcOH (Buffer A) & MeCN (Buffer B), 10-50% B). The products were pooled and lyophilized to provide Mpa-Br acetate salt as a free flowing crystalline solid. Analysis indicated 100% purity by RP-HPLC corresponding to fully substituted peptide conjugate Mpa-Br in an overall yield of 42.1%. Analysis of the conjugate for residual bromine (Br) via ion chromatography confirmed <0.1% Br indicating full substitution of the 4 arm bromoacetimide-PEG tetramer. Additional analysis of the Mpa-Br acetate salt was also carried out by SCX chromatography wherein the purity of the Mpa-Br acetate salt was found to be 90.0%.

Trytophan Fluorescence Spectroscopy:

Ligand and receptor interaction. A 2× concentration of each ligand (parental Vasculotide and MPA-Br) was prepared in 25 µL and mixed with 25 µL of a 2× concentration of Tie2Fc receptor to generate a 1× concentration of ligand and receptor in a final volume of 50 µL. The concentrations of ligand should be high enough to reach binding saturation of the receptor. Samples were read at ambient temperature by a SpectraMaxM2 plate reader set an excitation wavelength to 295 nm, a starting emission wavelength scan at 360 nm, an end emission wavelength scan at 450 nm with a set read interval of 10 nm and an auto mix for 5 seconds prior to reading. Data was compiled using SoftMax and analyzed using Prism.

Receptors and Ligands. Recombinant receptors were purchased from R&D Systems (recombinant human Tie-2Fc (R&D Systems), recombinant mouse Tie-2Fc (R&D Systems), recombinant rat Tie2-FC (R&D Systems) and recombinant cynomolgus monkey Tie2-FC (SinoBiological). Ligands were manufactured by Bachem (parental Vasculotide and MPA-Br). The negative IgG-FC control was sourced from R&D Systems. Both receptor and ligands were resuspended in DPBS (GE Life Sciences-HyClone).

Tie2 Phosphorylation—HUVEC:

Human umbilical vein endothelial cells (HUVECs) were seeded on 100 mm tissue culture plates in complete endothelial basal media (EBM)(Lonza) supplemented with 'EGM single quots' (Lonza) in 20% $O_2$, 5% $CO_2$ and 37° C. humidified chamber according to manufacturer's recommendations. Cells that had reached 90% confluence were simulated for 15 minutes with the specified concentrations of parental Vasculotide, MPA-Br or Angiopoietin-1 (R&D Systems) in complete EBM media. Following the 15 minute stimulation, cells were placed on ice and washed twice in ice cold PBS. Cell lysates were prepared for use in IC12 lysis buffer (1% NP-40, 20 mM Tris (pH 8.0), 137 mM NaCl, 10% Glycerol, 2 mM EDTA, 1 mM activated sodium orthovanadate). BCA protein concentration kit was used to measure protein concentration of each lysate as per manufacturer's instructions (Thermo Scientific). Samples were subjected to ELISAs that measured phosphorylated Tie2 and total Tie2 levels according to the manufacturers protocol. 20 µg or 5 µg of protein from each sample was loaded in duplicate for phosphorylated Tie2 and total Tie2 readings respectively. Phosphorylated Tie2:total Tie2 ratios were determined for each sample. The level of Tie2 phosphorylation for all treatment groups were then normalized to that of the no treatment group (NT, complete EBM only) in each experiment.

MAPK Phosphorylation—HUVEC:

HUVECs were cultured as above. Lyates were prepared in (1 mM EDTA, 0.5% Triton X-100, 6M urea, 5 mM NaF, 100 uM PMSF, 25 mM sodium pyrophosphate, 1 mM sodium orthovanadate, pH 7.2-7.4, 1× cOmplete™ mini EDTA-free protease inhibitor). BCA protein concentration kit was used to measure protein concentration of each lysate as per manufacturer's instructions (Thermo Scientific). Samples were subjected to ELISAs that measured phosphorylated MAPK and total MAPK levels according to the manufacturer's protocol (R&D Systems). 20 µg or 10 µg of protein from each sample was loaded in duplicate for phosphorylated MAPK and total MAPK readings respectively. Phosphorylated MAPK:total MAPK ratios were determined for each sample. The level of MAPK phosphorylation for all treatment groups were then normalized to that of the no treatment group (NT, EBM only) in each experiment.

Tie2 Phosphorylation—HMVEC$^{Tert}$:

Human microvascular endothelial cells (dermal origin) immortalized with human telomerase reverse transcriptase/catalytic subunit (tert), Shao and Guo (2004) were seeded on 100 mm tissue culture plates in complete endothelial basal media-2 (EBM-2)(Lonza) and were cultured in 20% $O_2$, 5% $CO_2$ and 37° C. humidified chamber. Growth media consisted of EBM-2, supplemented with 10% fetal bovine serum, 1× pen/strep, 1 ug/ml hydrocortisone and 100 ng/ml EGF. Cells that had reached 90% confluence were simulated for 15 minutes with the specified concentrations of parental Vasculotide, MPA-Br or Angiopoietin-1 in complete EBM-2 media. Following the 15 minute stimulation, cells were placed on ice and washed twice in ice cold PBS. Cell lysates were prepared for use in IC12 lysis buffer (1% NP-40, 20 mM Tris (pH 8.0), 137 mM NaCl, 10% Glycerol, 2 mM EDTA, 1 mM activated sodium orthovanadate). BCA protein concentration kit was used to measure protein concentration of each lysate. Samples were subject to ELISA measuring pYTie2 and total Tie2 concentration. 20 µg of protein from each sample were loaded to each well, each sample was run in duplicate. Relative pTie2 to total Tie2 ratios were determined for each sample. The level of Tie-2 phosphorylation in each treatment group was normalized to that of EBM-treated group in each experiment.

Tie2 Phosphorylation—Primary Mouse Lung Microvascular Endothelial Cells

Primary mouse lung endothelial cells (Cell Biologics) were seeded on 100 mm tissue culture plates in complete endothelial basal media (EBM)(Lonza) supplemented with 'EGM single quots' (Lonza). Cells that had reached 90% confluence were simulated for 15 minutes with the specified concentrations of parental Vasculotide, MPA-Br or Angiopoietin-1 (R&D systems) in complete EBM media. Following the 15 minute stimulation, cells were placed on ice and washed twice in ice cold PBS. Cell lysates were prepared for use in 1012 lysis buffer (1% NP-40, 20 mM Tris (pH 8.0), 137 mM NaCl, 10% Glycerol, 2 mM EDTA, 1 mM activated sodium orthovanadate). BCA protein concentration kit was used to measure protein concentration of each lysate as per manufacturer's instructions (Thermo Scientific). Samples were subjected to ELISAs that measured phosphorylated Tie2 and total Tie2 levels according to the manufacturer's protocol (mouse Tie2, R&D Systems). 50 µg or 5 µg of protein from each sample was loaded in triplicate for phosphorylated Tie2 and total Tie2 readings respectively. Phosphorylated Tie2:total Tie2 ratios were determined for each sample. The level of Tie2 phosphorylation for all treatment groups was then normalized to that of the no treatment group (NT, complete EBM only) in each experiment.

Tie2 Phosphorylation—Primary Rat Glomerular Endothelial Cells:

Rat primary glomerular endothelial cells (Cell Biologics) were grown in Complete rat endothelial cell medium/w kit (Cell Biologics) in 20% $O_2$, 5% $CO_2$ and 37° C. humidified chamber and split 1:3 once reaching 80-90% confluency. To examine the activation of Tie2 by MPA-Br in rat kidney glomerular endothelial cells, 95-100% confluent cells were stimulated with indicated concentrations of the test agent in serum-containing media for 15 minutes. Human Ang-1 (R&D Systems) was used as positive control. Cell lysates were collected using lysis buffer IC12 (detailed above) recommended in Human phospho-Tie-2 ELISA kit (R&D Systems), tyrosine-phosphorylated Tie2 and total Tie2 were measured using ELISA (Human phospho-Tie2 and total-Tie2 ELISA kits, R&D Systems) with substitution of capture antibody validated for rat Tie2. Mouse anti-Tie2 antibody (BD Pharmingen™) and rabbit TEK polyclonal antibody (MyBioSource) were used as capture antibody in pTie2 and total Tie2 ELISA, respectively. The level of Tie2 phosphorylation for all treatment groups were then normalized to that of the no treatment group (NT, complete rat endothelial cell medium) in each experiment.

Tie2 Phosphorylation—Primary Canine Aorta Endothelial Cells:

Canine primary aortic endothelial cells (Cell Biologics) were grown in Complete canine endothelial cell medium/w kit (Cell Biologics) in 20% $O_2$, 5% $CO_2$ and 37° C. humidified chamber and split 1:3 once reaching 80-90% confluency. Tie2 activation studies performed on primary cynomolgus monkey glomerular endothelial cells were performed according to approaches detailed above for the rat primary glomerular endothelial cell studies.

Tie2 Phosphorylation—Primary Cynomolgus Monkey Glomerular Endothelial Cells:

Primary cynomolgus monkey glomerular endothelial cells (Cell Biologics) were cultured according to details provided above for HMVEC$^{tert}$. Tie2 activation studies performed on primary cynomolgus monkey glomerular endothelial cells were performed according to approaches detailed above for the rat primary glomerular endothelial cell studies.

Cutaneous Histamine Challenge:

10-week old male FVB mice were purchased from Jackson Laboratories. Mice were housed in a Vivarium on a standard light:dark cycle and were given free access to food and water. On day 0 mice were anesthetized with isoflurane and the entire dorsal area was shaved with an electric shaver. Residual hair was removed via application of depilatory cream. Residual cream was removed with sterile gauze and water. On day 4 mice received either vehicle control (sterile PBS), parental Vasculotide, or MPA-Br as a 200 ul intraperitoneal injection. One hour following delivery of PBS/parental Vasculotide/MPA-Br mice were placed under isoflurane anesthetic at which point 100 ul of 1% Evans blue dye (contained in sterile PBS) was delivered intravenously via the tail vein. Immediately following Evans blue dye administration, and while still under anesthesia, a single PBS injection (dorsal, intradermal, 50 ul) and three equally spaced histamine injections (dorsal, intradermal, 1.25 ug contained in 50 ul) were applied. Once the intradermal injections were complete, the mice were removed from anesthesia and were placed back into their housing cages for 25 minutes.

Cardiac transperfusion

After 25 minutes of exposure to histamine the mice were placed under anesthesia with an appropriate volume of 2.5% avertin (100 ul/10 g body weight via intraperitoneal injection). Once a deep plane of anesthesia was produced the mice were place and secured in a supine position, the chest was surgically opened, the heart was exposed and a catheter terminating in a 23 gauge needle was inserted into the left ventricle. Once the catheter was securely in place, a cut in the right atria was performed and 25 ml of cold PBS was delivered, via the catheter at 100 mmHg to flush out all intravascular Evans blue dye. Once a mouse was effectively perfused the dorsal skin was surgically removed. Four, 12 mm skin biopsies were collected (1PBS, 3 histamine) for each mouse using a standardized skin punch. In all cases, the biopsy that received PBS served as a baseline control for that individual mouse.

Quantification of Evans blue dye extravassation

Skin biopsies were placed in labelled tubes and placed in a 60 degree Celsius oven for 16 hrs to removed all moisture. Desiccated skin biopsies were weighed, placed in tubes containing 1.5 ml of formamide and then placed in a 60 degree Celsius water bath for 72 hours. After 72 hours the tubes were centrifuged at 500 RCF and a 100 ul sample was removed to a flat bottom 96-well microtiter plate for measurement at 620 nm and 405 nm. An Evans blue dye standard curve encompassing high and low experimental data points was constructed such that the amount of Evans blue dye extravassation (ug/g of skin) could be calculated.

Influenza Study:

Experimental design.

Fourteen-week old C57BL/6J mice were purchased (Jackson Laboratories). Mice were housed in a Vivarium on a standard light:dark cycle and were given free access to food and water. For all experiments, mice were sedated with 5% isoflurane and infected intranasally with influenza virus (see Virus section, below) diluted in PBS to a final volume of 80 uL. After infection, mice were separated into weight-matched control and treatment groups; each experimental treatment arm used ten mice per group and mice were infected with 64 HAU of influenza virus, which caused 100% mortality by day 7. The following groups were included: mice that received the influenza virus alone (Flu), infected mice that also received parental Vasculotide (500 ng in 0.1 mL PBS by intraperitoneal injection) or MPA-Br (200 ng or 31.25 ng in 0.1 mL PBS by intraperitoneal injection). Treatment with parental Vasculotide or MPA-Br commenced 48 hours post infection and was given once every 24 hrs for the duration of the study. Control mice (Flu) received a daily intraperitoneal injection of 0.1 mL PBS starting at 48 hrs post infection for the duration of the study.

Virus.

Influenza A virus HKx31 (H3N2) was originally obtained from Dr. Tania Watts and propagated in accordance with Szretter, K. J., Balish, A. L. & Katz, J. M., 2006. Viral titer from culture supernatant was determined by performing a standard plaque-forming assay in MDCK (Madin-Darby Canine Kidney) cells or by measuring agglutination of sheep red blood cells (hemagglutinin units, HAU).

Pulse oximetry measurements.

Arterial oxygen saturation was measured using the Mouse Ox Plus device and software (Starr Life Sciences, Oakmont, Pa.) on awake (non-anesthetized) mice using either the small collar clips for C57BL/6J. For C57BL/6J mice, a chemical depilatory cream was used to remove hair around the base of the neck several days before infection. For SO2 measurements, mice were allowed to acclimate to the collar clip for several minutes in their home cage before recording the maximal SO2 measurement.

Activity Scoring Guidelines

Mice were observed twice daily, weighed once daily, and assigned an activity score from 1 to 5. To receive a score of 5, the mouse must exhibit a normal active and curious behavior. It moves about and stands upright at the sides of the cage. For a score of 4, the mouse is not quite as active. It does not stand up as often and prefers to stay in the corners of the cage. For a score of 3, the mouse is less active, and when it moves, it often stops and sits. It stays in the nest corner. For a score of 2, the mouse moves only when touched, and only for a short distance. It preferably hides in the nest corner. Finally, for a score of 1, the mouse is moribund. Activity scores of 5-3 are deemed acceptable. Mice having an activity score of 2 were monitored closely, and if activity decreased below a score of 2, they were sacrificed. Additionally, mice that experience weight loss of more than 30%, regardless of an otherwise acceptable activity score, were euthanized.

Generic Reaction Methods for Michael Additions

Activated PEG tetramer (such as vinyl sulfone or acrylate) (117-118 mg, 1equiv.) and Mpa-peptide (100 mg, 1.5 equiv.) were added to 50 ml a round bottom flask protected from light and PBS (pH 6.5*, 20 ml) was added for a final peptide concentration of 5 mg/ml. The reaction was stirred at RT, the pH verified using a pH meter and the progress of the reaction monitored by HPLC at various time intervals.

The reaction mixture was acidified to pH 3.5 before purification using the following steps:

Step 1 Flash LC:
  Column: Reverse Phase C18, Fuji, 200 Å, 40 g column 30 μm (custom packed).
  Gradient profile: 10-100% B in 63 minutes
  Eluents: Eluent A=0.1% TFA in water
  Eluent B=0.1% TFA in 60% acetonitrile, 40% water
  Detection: UV (λ=210 nm/254 nm)
  Column Temperature: RT
  Flow Rate: 40 mL/min Step 2 Preparative HPLC:
  Column: Reverse Phase C18, Daiso Bio C18, 200 Å, 10 μm 25 mm×250 mm (custom packed).
  Gradient profile: 45-100% B in 77 minutes
  Eluents: Eluent A=0.1% HFBA in 3% acetonitrile in water
  Eluent B=0.1% HFBA in 60% acetonitrile, 40% water
  Detection: UV (λ=210 nm)
  Column Temperature: RT
  Flow Rate: 30 mL/min Step 3 Preparative HPLC:
  Column: Reverse Phase C18, Daiso Bio C18, 200 Å, 10 μm 25 mm×25 mm (custom packed).
  Gradient profile: 40-100% B in 84 minutes
  Eluents: Eluent A=0.1% TFA in water
  Eluent B=0.1% TFA in 60% acetonitrile, 40% water.

Yield of vinyl sulfone PEG conjugate is 48 mgs and acrylate-PEG conjugate 15.2 mg, both as TFA salts.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Berge S M, Bighley L D, Monkhouse D C, "Pharmaceutical salts" *J Pharm Sci.* 1977 January; 66(1):1-19.

Bourdeau A, Van Slyke P, Kim H, Cruz M, Smith T, Dumont D J, "Vasculotide, an Angiopoietin-1 mimetic, ameliorates several features of experimental atopic dermatitis-like disease" *BMC Res Notes.* 2016 May 28; 9:289.

Brkovic A, Pelletier M, Girard D, Sirois M G, "Angiopoietin chemotactic activities on neutrophils are regulated by PI-3K activation" *J Leukoc Biol.* 2007 April, 81(4):1093-101.

Cho C H, Kammerer R A, Lee H J, Steinmetz M O, Ryu Y S, Lee S H, Yasunaga K, Kim K T, Kim I, Choi H H, Kim W, Kim S H, Park S K, Lee G M, Koh G Y, "COMP-Ang1: a designed angiopoietin-1 variant with nonleaky angiogenic activity" *Proc Natl Acad Sci USA.* 2004 Apr. 13; 101(15):5547-52.

Eichenfield L F, Hanifin J M, Beck L A, Lemanske R F Jr, Sampson H A, Weiss S T, Leung D Y, "Atopic dermatitis and asthma: parallels in the evolution of treatment" *Pediatrics.* 2003 March, 111(3):608-16.

Gruber B L, Marchese M J, Kew R, "Angiogenic factors stimulate mast-cell migration" *Blood.* 1995 Oct. 1; 86(7):2488-93.

Kim W, Moon S O, Lee S Y, Jang K Y, Cho C H, Koh G Y, Choi K S, Yoon K H, Sung M J, Kim D H, Lee S, Kang K P, Park S K, "COMP-angiopoietin-1 ameliorates renal fibrosis in a unilateral ureteral obstruction model" *J Am Soc Nephrol.* 2006 September; 17(9):2474-83.

Kuiken T, Taubenberger J K, "Pathology of human influenza revisited" *Vaccine.* 2008 Sep. 12; 26 Suppl 4:D59-66.

Maliba R, Brkovic A, Neagoe P E, Villeneuve L R, Sirois M G, "Angiopoietin-mediated endothelial P-selectin translocation: cell signaling mechanisms" *J Leukoc Biol.* 2008 February; 83(2):352-60.

Murdoch C, Tazzyman S, Webster S, Lewis C E, "Expression of Tie-2 by human monocytes and their responses to angiopoietin-2" *J Immunol.* 2007 Jun. 1; 178(11):7405-11.

Parikh S M, "Dysregulation of the angiopoietin-Tie-2 axis in sepsis and ARDS" *Virulence.* 2013 Aug. 15; 4(6):517-24.

Riley C M, Fuegy P W, Firpo M A, Shu X Z, Prestwich G D, Peattie R A "Stimulation of in vivo angiogenesis using dual growth factor-loaded crosslinked glycosaminoglycan hydrogels" *Biomaterials.* 2006 December, 27(35):5935-43.

Rübig E, Stypmann J, Van Slyke P, Dumont D J, Spieker T, Buscher K, Reuter S, Goerge T, Pavenstädt H1, Kümpers P, "The Synthetic Tie2 Agonist Peptide Vasculotide Protects Renal Vascular Barrier Function In Experimental Acute Kidney Injury" *Sci Rep.* 2016 Feb. 25; 6:22111.

Shao R, Guo X, "Human microvascular endothelial cells immortalized with human telomerase catalytic protein: a model for the study of in vitro angiogenesis" *Biochem Biophys Res Commun.* 2004 Sep. 3; 321(4):788-94.

Sturn D H, Feistritzer C, Mosheimer B A, Djanani A, Bijuklic K, Patsch J R, Wiedermann C J, "Angiopoietin affects neutrophil migration" *Microcirculation.* 2005 July-August; 12(5):393-403.

Sugiyama M G, Armstrong S M, Wang C, Hwang D, Leong-Poi H, Advani A, Advani S, Zhang H, Szaszi K, Tabuchi A, Kuebler W M, Van Slyke P, Dumont D J, Lee W L, "The Tie2-agonist Vasculotide rescues mice from influenza virus infection" *Sci Rep.* 2015 Jun. 5; 5:11030.

Szretter K J, Balish A L, Katz J M, "Influenza: propagation, quantification, and storage" *Curr Protoc Microbiol.* 2006 December; Chapter 15:Unit 15G.1.

Thamm K, Njau F, Van Slyke P, Dumont D J, Park J K, Haller H, David S, "Pharmacological Tie2 activation in kidney transplantation" *World J Transplant.* 2016 Sep. 24; 6(3):573-82.

Tournaire R, Simon M P, le Noble F, Eichmann A, England P, Pouysségur J, "A short synthetic peptide inhibits signal transduction, migration and angiogenesis mediated by Tie2 receptor" *EMBO Rep.* 2004 March; 5(3):262-7.

Van Slyke P, Alami J, Martin D, Kuliszewski M, Leong-Poi H, Sefton M V, Dumont D "Acceleration of diabetic wound healing by an angiopoietin peptide mimetic" *Tissue Eng Part A.* 2009 June; 15(6):1269-80.

Wu X, Zhao R, Li Z, Yao M, Wang H, Han J, Qu S, Chen X, Qian L, Sun Y, Xu Y, Gu J, "A novel small peptide as a targeting ligand for receptor tyrosine kinase Tie2" *Biochem Biophys Res Commun.* 2004 Mar. 19; 315(4):1004-10.

Zhang Z G, Zhang L, Croll S D, Chopp M, "Angiopoietin-1 reduces cerebral blood vessel leakage and ischemic lesion volume after focal cerebral embolic ischemia in mice" *Neuroscience.* 2002; 113(3):683-7.

The invention claimed is:

1. A compound of formula (I),

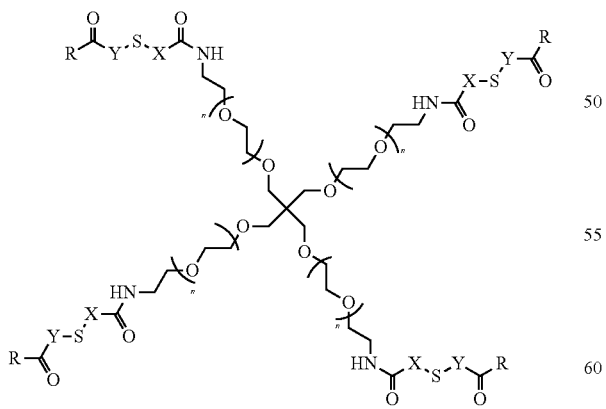

wherein n is an integer from about 25 to about 100, each X is independently or simultaneously $(C_1\text{-}C_{20})$-alkylene or $(C_2\text{-}C_{20})$-alkenylene, each of which is optionally substituted with one or more of halo, amino, hydroxy, $(C_1\text{-}C_6)$-alkyl, $(C_1\text{-}C_6)$-alkoxy, $(C_6\text{-}C_{10})$-aryl, or $(C_5\text{-}C_{10})$-heteroaryl;

each Y is independently or simultaneously $(C_1\text{-}C_{20})$-alkylene or $(C_2\text{-}C_{20})$-alkenylene, each of which is optionally substituted with one or more of halo, amino, hydroxy, $(C_1\text{-}C_6)$-alkyl, $(C_1\text{-}C_6)$-alkoxy, $(C_6\text{-}C_{10})$-aryl, or $(C_5\text{-}C_{10})$-heteroaryl; and R is a T7 peptide having the amino acid sequence set forth as SEQ ID NO:1, a GA3 peptide having the amino acid sequence set forth as SEQ ID NO:2, a T4 peptide having the amino acid sequence set forth as SEQ ID NO:3, a T6 peptide having the amino acid sequence set forth as SEQ ID NO:4 or a T8 peptide having the amino acid sequence set forth as SEQ ID NO:5; or a pharmaceutically acceptable salt thereof.

2. The compound of claim 1, wherein R is a T7 peptide having the amino acid sequence set forth as SEQ ID NO: 1.

3. The compound of claim 1, wherein n is an integer from about 40 to about 70, from about 48 to about 65, or about 55.

4. The compound of claim 1, wherein X is independently or simultaneously $(C_1\text{-}C_6)$-alkylene or $(C_2\text{-}C_6)$-alkenylene.

5. The compound of claim 1, wherein Y is independently or simultaneously $(C_1\text{-}C_6)$-alkylene or $(C_2\text{-}C_6)$-alkenylene.

6. The compound of claim 1, wherein Y is derived from thioglycolic acid, 2-Mercaptopropionic acid, 4-Mercaptobutyric acid, 6-Mercaptohexanoic acid, 8-Mercaptooctanic acid, 11-Mercaptoundecanoic acid, 12-Mercaptododecanoic acid, or 16-Mercaptohexadecanoic acid.

7. The compound of claim 1, wherein the compound of formula (I) is

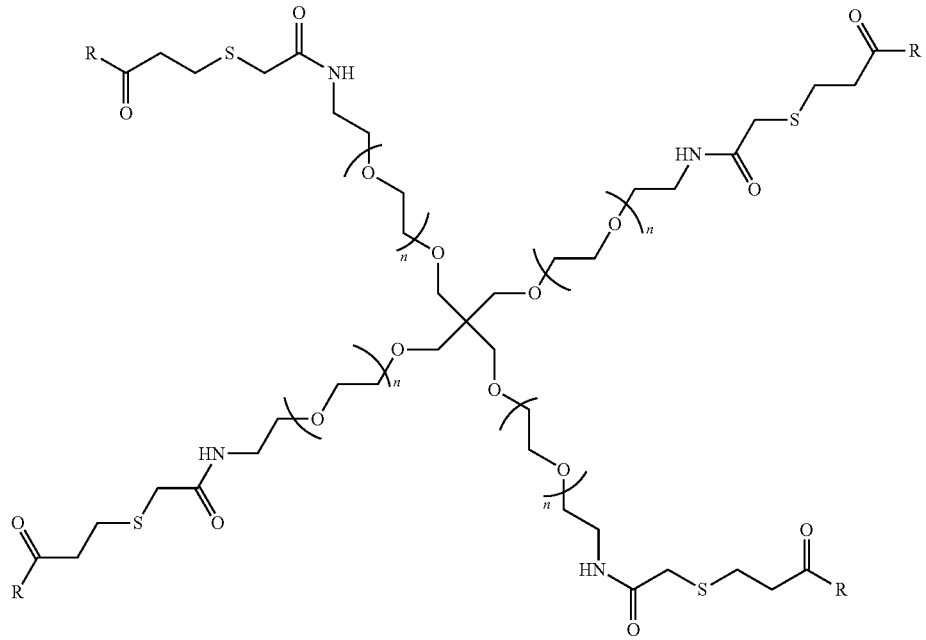

wherein
n is an integer between about 50-60 or about 55; and
R has the amino acid sequence set forth in SEQ ID NO: 1;
or a pharmaceutically acceptable salt thereof.

8. A pharmaceutical composition comprising the compound of claim 1 and a pharmaceutically acceptable carrier.

9. A pharmaceutical composition comprising a compound according to claim 7 and a pharmaceutically acceptable carrier, the pharmaceutical composition suitable for inhalation and/or topical, systemic, oral, intranasal, or parenteral administration.

10. A composition comprising (a) the compound of claim 1 and (b) an antiviral agent.

11. The composition of claim 10, wherein the antiviral agent is amantadine, rimantadine, zanamivir, peramivir, viramidine, ribavirin or oseltamivir.

12. A biomaterial into which is incorporated a compound of claim 1; wherein the biomaterial is selected from the group consisting of Matrigel, a skin substitute and a cross-linked glycosaminoglycan hydrogel.

13. A method of making a compound of formula (I), the method comprising
(i) reacting a peptide which is a T7 peptide having the amino acid sequence set forth as SEQ ID NO:1, a GA3 peptide having the amino acid sequence set forth as SEQ ID NO:2, a T4 peptide having the amino acid sequence set forth as SEQ ID NO:3, a T6 peptide having the amino acid sequence set forth as SEQ ID NO:4 and/or a T8 peptide having the amino acid sequence set forth as SEQ ID NO:5 or retro-inverso peptides thereof, with a thiol compound of the formula (II)

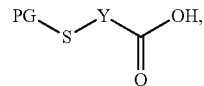

to obtain a compound of the formula (III) or a salt thereof

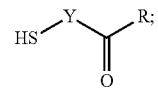

(ii) reacting the compound of the formula (III) with a PEG-tetramer of the formula (IV)

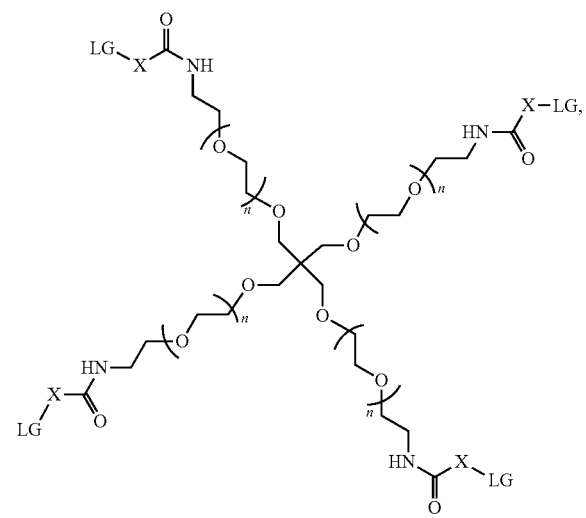

to obtain a compound of the formula (I) as defined in claim 1, or pharmaceutically acceptable salt thereof;

wherein the variables n, X and Y are as in claim 1, LG is a suitable leaving group and PG is H or a suitable protecting group.

14. The method of claim 13, wherein the suitable leaving group is halo, a tosylate or a mesylate.

15. The method of claim 14, wherein the halo is bromo.

16. The method of claim 14, wherein the suitable protecting group is trityl.

17. A method of stimulating angiogenesis comprising administering the compound of claim 1 at a site in a subject in need thereof.

18. A method of decreasing vascular permeability comprising administering the compound of claim 1 at a site of leaky vessels in a subject in need thereof.

19. A method of protecting endothelial cells comprising administering the compound of claim 1 to a subject in need thereof.

20. A method of stimulating healing of a wound comprising administering the compound of claim 1 to a subject in need thereof.

21. The method of claim 20, wherein the wound is a diabetic ulcer or wherein the wound is selected from the group consisting of a decubitus ulcer, a pressure ulcer, a surgical incision, a traumatic tissue injury, a burn and a skin graft.

22. A method of treating atopic dermatitis, asthma, allergic rhinitis, leukemia of eosinophil and/or basophil origin, inflammatory bowel disease or a parasitic infection by inhibiting the expansion of CFU-G cells in a subject comprising administering the compound of claim 1 to the subject.

23. A method of treating primary viral pneumonia or bacterial pneumonia that occurs simultaneous with or following influenza infection comprising administering the compound of claim 1 to an animal in need thereof.

24. The method of claim 23, further comprising administering an antiviral agent concurrently or sequentially.

25. The method of claim 24, wherein the antiviral agent is amantadine, rimantadine, zanamivir, peramivir, viramidine, ribavirin or oseltamivir.

26. The method of claim 23, wherein the animal is a human with primary viral pneumonia.

* * * * *